United States Patent [19]

Oxford et al.

[11] Patent Number: 4,808,581
[45] Date of Patent: Feb. 28, 1989

[54] IMIDAZOLYL- INDOLYLPROPANONES AS 5-HT₃ RECEPTOR ANTAGONISTS

[75] Inventors: Alexander W. Oxford, Hertfordshire; David J. Cavalla, London, both of England

[73] Assignee: Glaxo Group Limited, United Kingdom

[21] Appl. No.: 147,204

[22] Filed: Jan. 22, 1988

Related U.S. Application Data

[63] Continuation-in-part of Ser. No. 99,405, Sep. 22, 1987, abandoned, which is a continuation of Ser. No. 26,179, Mar. 16, 1987, abandoned.

[30] Foreign Application Priority Data

Mar. 17, 1986 [GB] United Kingdom ................ 8606579
Jul. 23, 1986 [GB] United Kingdom ................ 8617995
Jan. 23, 1987 [GB] United Kingdom ................ 8701494

[51] Int. Cl.⁴ .................... A61K 31/55; C07D 403/06
[52] U.S. Cl. .................... 514/212; 514/323; 514/397; 540/603; 546/201; 548/336
[58] Field of Search ............ 548/336; 514/397, 212, 514/323; 546/201; 540/603

[56] References Cited

U.S. PATENT DOCUMENTS 4,619,941 10/1986 Wright et al. .................... 514/397
4,695,578 9/1987 Coates et al. .................... 548/336 X

FOREIGN PATENT DOCUMENTS 3901 9/1979 European Pat. Off. ............ 548/336
73663 3/1983 European Pat. Off. ............ 548/336
3430284 2/1986 Fed. Rep. of Germany ...... 546/201
2045244 10/1980 United Kingdom ................ 548/336
2169292 7/1986 United Kingdom .

OTHER PUBLICATIONS

P. G. Baraldi et al., Chem. Abs., 1981, 94:84484n (Farmaco, Ed. Sci., 1980, 35(8), 698-705).

Primary Examiner—Richard A. Schwartz
Attorney, Agent, or Firm—Bacon & Thomas

[57] ABSTRACT

The invention relates to compounds of formula (I):

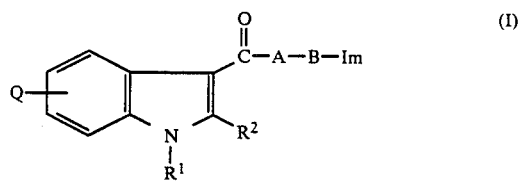

and physiologically acceptable salts or solvates thereof, wherein Im represents an imidazolyl group of formula:

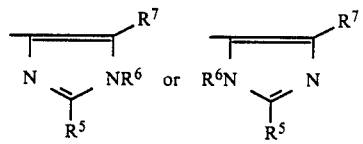

and the various substituents are defined hereinbelow.

The compounds are potent and selective antagonists of the effect of 5-HT at 5-HT₃ receptors and are useful, for example, in the treatment of psychotic disorders, anxiety, and nausea and vomiting.

23 Claims, No Drawings

IMIDAZOLYL- INDOLYLPROPANONES AS 5-HT$_3$ RECEPTOR ANTAGONISTS

This application is a continuation-in-part of application Ser. No. 099,405, filed Sept. 22, 1987, now abandoned, which is s continuation of Ser. No. 026,179, filed Mar. 16, 1987, which is abandoned.

This invention relates to heterocyclic compounds, to processes for their preparation, to pharmaceutical compositions containing them and to their medical use. In particular the invention relates to compounds which act upon 5-hydroxytryptamine (5-HT) receptors of the type located on terminals of primary afferent nerves.

Compounds having antagonist activity at 'neuronal' 5-HT receptors of the type located on primary afferent nerves have been described previously.

Thus for example published UK Specification No. 2153821 discloses tetrahydrocarbazolones of the general formula

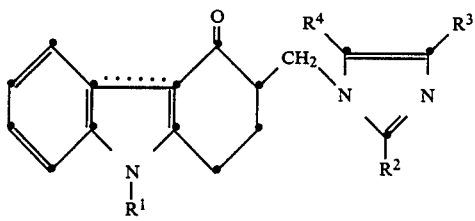

wherein $R^1$ represents a hydrogen atom or a $C_{1-10}$alkyl, $C_{3-7}$cycloalkyl, $C_{3-6}$alkenyl, phenyl or phenyl $C_{1-3}$alkyl group, and one of the groups represented by $R^2$, $R^3$ and $R^4$ is a hydrogen atom or a $C_{1-6}$alkyl, $C_{3-7}$cycloalkyl, $C_{2-6}$alkenyl or phenyl$C_{1-3}$alkyl group and each of the other two groups, which may be the same or different, represents a hydrogen atom or a $C_{1-6}$ alkyl group.

We have now found a novel group of compounds which differ in structure from those described previously, and which are potent antagonists of the effect of 5-HT at 5-HT 'neuronal' receptors, and possess an advantageous profile of activity.

Thus the present invention provides an indole of the general formula (I):

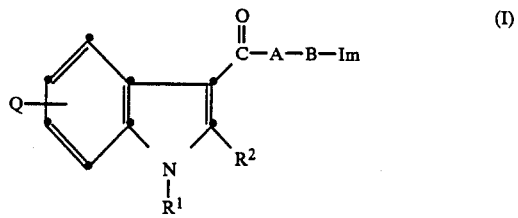

and physiologically acceptable salts and solvates thereof, wherein Im represents an imidazolyl group of formula:

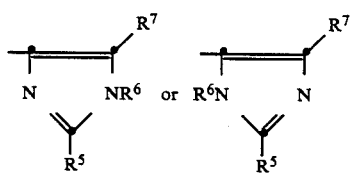

$R^1$ represents a hydrogen atom or a group selected from $C_{1-6}$alkyl, $C_{3-6}$ alkenyl, $C_{3-10}$ alkynyl, $C_{3-7}$ cycloalkyl, $C_{3-7}$cycloalkyl$C_{1-4}$alkyl, phenyl, phenyl$C_{1-3}$alkyl, —$CO_2R^8$, —$COR^8$, —$CONR^8R^9$ or —$SO_2R^8$ (wherein $R^8$ and $R^9$, which may be the same or different, each represents a hydrogen atom, a $C_{1-6}$ alkyl or $C_{3-7}$ cycloalkyl group, or a phenyl or phenyl$C_{1-4}$alkyl group, in which the phenyl group is optionally substituted by one or more $C_{1-4}$ alkyl, $C_{1-4}$ alkoxy or hydroxy groups or halogen atoms, with the proviso that $R^8$ does not represent a hydrogen atom when $R^1$ represents a group —$CO_2R^8$ or —$SO_2R^8$); $R_2$ represents a hydrogen atom or a $C_{1-6}$ alkyl, $C_{3-6}$ alkenyl, $C_{3-7}$ cycloalkyl, phenyl or phenyl$C_{1-3}$alkyl group; A-B represents the group $R^3R^4C$-$CH_2$ or $R^3C$=CH; $R^3$ and $R^4$, which may be the same or different, each represents a hydrogen atom or a $C_{1-6}$ alkyl group; one of the groups represented by $R^5$, $R^6$ and $R^7$ is a hydrogen atom or a $C_{1-6}$alkyl, $C_{3-7}$cycloalkyl, $C_{3-6}$ alkenyl, phenyl or phenyl$C_{1-3}$alkyl group, and each of the other two groups, which may be the same or different, represents a hydrogen atom or a $C_{1-6}$ alkyl group; Q represents a hydrogen atom or a halogen atom or a hydroxy, $C_{1-4}$alkoxy, phenyl$C_{1-3}$alkoxy or $C_{1-6}$ alkyl group or a group —$NR^{10}R^{11}$ or —$CONR^{10}R^{11}$ (wherein $R^{10}$ and $R^{11}$, which may be the same or different, each represents a hydrogen atom or a $C_{1-4}$ alkyl or $C_{3-4}$alkenyl group, or together with the nitrogen atom to which they are attached form a saturated 5 to 7 membered ring; and with the proviso that when A-B represents the group $R^3C$=CH, Q represents a hydrogen atom and $R^1$ represents a hydrogen atom or a $C_{1-6}$ alkyl, $C_{3-6}$ alkenyl, $C_{3-10}$ alkynyl, $C_{3-7}$ cycloalkyl, $C_{3-7}$ cycloalkyl$C_{1-4}$alkyl, phenyl or phenyl $C_{1-3}$alkyl group.

All optical isomers of compounds of general formula (I) and their mixtures including the racemic mixtures thereof, and all the geometric isomers of compounds of formula (I), are embraced by the invention.

Referring to the general formula (I), the alkyl groups represented by $R^1,R^2,R^3,R^4,R^5,R^6,R^7,R^8,R^9,R^{10},R^{11}$ and Q may be straight chain or branched chain alkyl groups for example, methyl, ethyl, propyl, prop-2-yl, butyl or but-2-yl, and, in the case of $R^1$ to $R^9$ and Q, pentyl, pent-3-yl or hexyl groups.

A $C_{3-6}$ alkenyl group may be, for example, a propenyl or butenyl group. A $C_{3-10}$ alkynyl group, may be, for example, a prop-2-ynyl or oct-2-ynyl group. It will be appreciated that when $R^1$ represents a $C_{3-6}$alkenyl or $C_{3-10}$ alkynyl group, or $R^{10}$ or $R^{11}$ represents a $C_{3-4}$ alkenyl group, the double or triple bond may not be adjacent to the nitrogen atom. A phenyl$C_{1-3}$alkyl group (as such, or as part of a phenyl $C_{1-3}$ alkoxy group) may be, for example, a benzyl, phenethyl or 3-phenylpropyl group. A $C_{3-7}$cycloalkyl group, either alone or as part of a $C_{3-7}$cycloalkyl$C_{1-4}$alkyl group, may be, for example, a cyclopropyl, cyclobutyl, cyclopentyl, cyclohexyl or cycloheptyl group.

When $R^1$ represents a $C_{3-7}$cycloalkyl$C_{1-4}$alkyl group, the alkyl moiety may be, for example, a methyl, ethyl, propyl, prop-2-yl or butyl group. When Q represents a $C_{1-4}$ alkoxy group it may be, for example, a methoxy group. When Q represents a halogen atom it may be, for example a fluorine, chlorine or bromine atom. The substituent Q may be at the 4, 5, 6 or 7 position of the indole moiety.

According to one aspect, the invention provides compounds of formula (I) as represented by the formula (Ia):

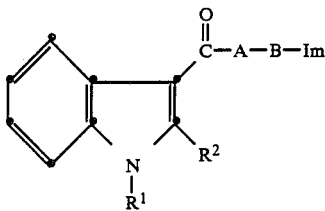

(Ia)

in which $R^1$ represents a hydrogen atom or a $C_{1-6}$ alkyl, $C_{3-6}$ alkenyl, $C_{3-10}$ alkynyl, $C_{3-7}$ cycloalkyl, $C_{3-7}$ cycloalkylC$_{1-4}$ alkyl, phenyl or phenylC$_{1-3}$ alkyl group, and $R^2$, A-B and Im are as defined in formula (I).

According to another aspect the invention provides compounds of formula (I) as represented by the formula (Ib):

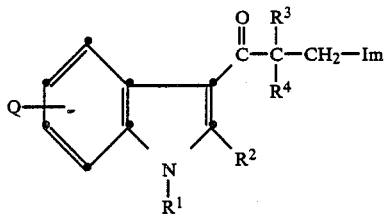

(Ib)

in which $R^1$ to $R^4$, Q and Im are as defined in formula (I), with the proviso that when Q represents a hydrogen atom, $R^1$ represents —$CO_2R^8$, —$COR^8$, —$CONR^8R^9$ or —$SO_2R^8$ According to yet another aspect, the invention provides compounds of formula (Ia) in which $R^1$ and $R^2$ each independently represent a hydrogen atom or a $C_{1-6}$ alkyl, $C_{3-6}$ alkenyl, $C_{3-7}$ cycloalkyl, phenyl or phenylC$_{1-3}$alkyl group; one of the groups represented by $R^5$, $R^6$ and $R^7$ is a hydrogen atom or a $C_{1-6}$ alkyl, $C_{3-7}$ cycloalkyl, $C_{3-6}$ alkenyl or phenyl $C_{1-3}$ alkyl group, and each of the other two groups, which may be the same or different, represents a hydrogen atom or a $C_{1-6}$ alkyl group; and A-B, $R^3$ and $R^4$ are as defined in formula (Ia).

A preferred group of compounds of formula (Ib) are those in which A-B represents $R^3R^4C$—$CH_2$, and $R^1$, $R^2$, $R^3$, $R^4$, $R^5$, $R^6$ and $R^7$ are as defined in formula (Ia).

A preferred class of compounds of formula (I) are those where $R^1$ represents a hydrogen atom or a $C_{1-3}$ alkyl (eg methyl or isopropyl), $C_{3-4}$ alkenyl (eg prop-2-enyl), $C_{3-4}$ alkynyl) (eg prop-2-ynyl), $C_{5-6}$cycloalkyl (eg cyclopentyl), $C_{5-6}$ cycloalkylmethyl (eg cyclopentylmethyl), benzyl, N,N-diC$_{1-3}$alkylcarboxamido (e.g. N,N-dimethylcarboxamido) or a $C_{1-3}$ alkoxycarbonyl (e.g. methoxycarbonyl) group. Most preferably $R^1$ represents a hydrogen atom or a $C_{1-3}$ alkyl, $C_{3-4}$alkenyl, $C_{3-4}$alkynyl, $C_{5-6}$ cycloalkyl or benzyl, N,N-diC$_{1-3}$alkylcarboxamido or $C_{1-3}$ alkoxycarbonyl group.

Another preferred class of compounds of formula (I) are those wherein $R^2$ represents a phenyl goup, or more preferably, a hydrogen atom or a $C_{1-3}$ alkyl (eg methyl) group.

Another preferred class of compounds of formula (I) are those wherein A-B represents CH=CH or $R^3R^4$—$CH_2$ where $R^3$ and $R^4$ each independently represent a hydrogen atom or a $C_{1-3}$ alkyl (eg methyl) group. A particularly preferred class of compounds are those in which A-B represents $R^3R^4$—$CH_2$ and $R^3$ and $R^4$ each independently represent a hydrogen atom or a methyl group. A further particularly preferred class of compounds are those in which $R^3$ and $R^4$ both represent hydrogen atoms.

A further preferred class of compounds of formula (I) are those wherein $R^5$ represents a $C_{1-3}$ alkyl (eg methyl) group or, more preferably, a hydrogen atom. $R^6$ preferably represents a $C_{1-3}$ alkyl (eg methyl), $C_{3-4}$ alkenyl (eg prop-2-enyl), benzyl or, more preferably, a hydrogen atom. $R^7$ preferably represents a hydrogen atom or a $C_{1-3}$ alkyl (eg methyl or n-propyl) group. When $R^5$ and $R^6$ represent hydrogen atoms, $R^7$ is preferably a $C_{1-6}$ alkyl, $C_{3-7}$ cycloalkyl, $C_{3-6}$ alkenyl, phenyl or phenylC$_{1-3}$ alkyl group, more particularly $C_{1-3}$ alkyl (eq methyl).

Another preferred class of compounds of formula (I) are those wherein Q represents a hydrogen atom, a halogen (e.g. fluorine) atom or a hydroxy, $C_{1-3}$alkoxy (e.g. methoxy) or $C_{1-3}$alkyl (e.g. methyl) group. More preferably Q represents a hydrogen or halogen (e.g. fluorine) atom or a $C_{1-3}$alkyl (e.g. methyl) group.

When Q is other than a hydrogen atom, it is preferably at the 5-, 6- or 7-position of the indole ring, more preferably the 5- or 7-position.

A preferred group of compounds of formula (Ia) are those in which $R^1$ represents a hydrogen atom or a $C_{1-3}$ alkyl, $C_{3-4}$ alkenyl, $C_{3-4}$alkynyl, $C_{5-6}$ cycloalkyl or benzyl group; $R^2$ represents a hydrogen atom or a $C_{1-3}$ alkyl group; A-B represents CH=CH or $R^3R^4C$-$CH_2$ where $R^3$ and $R^4$ each independently represent a hydrogen atom or a $C_{1-3}$ alkyl group; and $R^5$, $R^6$ and $R^7$ each independently represent a hydrogen atom or a $C_{1-3}$ alkyl group.

A particularly preferred group of compounds of formula (Ia) are those wherein $R^1$ represents a hydrogen atom or a methyl, prop-2-enyl or cyclopentyl group; $R^2$ represents a hydrogen atom or a methyl group; A-B represents $CR^3R^4$-$CH_2$ where $R^3$ and $R^4$ each independently represent a hydrogen atom or a methyl group; $R^5$ and $R^6$ each represent a hydrogen atom; and $R^7$ represents a hydrogen atom or a $C_{1-3}$ alkyl group, most preferably methyl.

A preferred group of compounds of formula (Ib) are those wherein $R^1$ represents a $C_{1-3}$ alkyl (e.g. methyl), N,N-diC$_{1-3}$alkylcarboxamido (e.g. N,N-dimethylcarboxamido) or $C_{1-3}$alkoxycarbonyl (e.g. methoxycarbonyl) group, more preferably a methyl group; $R^2$ represents a hydrogen atom; $R^3$ and $R^4$ both represent hydrogen atoms; $R^5$ and $R^6$ each represent a hydrogen atom; $R^7$ represents a hydrogen atom or $C_{1-3}$ alkyl group, more preferably a methyl group; and Q represents a hydrogen or halogen (e.g. fluorine) atom or a $C_{1-3}$ alkyl (e.g. methyl) group.

Particularly preferred compounds according to the invention are:
3-(5-methyl-1H-imidazol-4-yl)-1-(1-methyl-1H-indol-3-yl)-1-propanone; 2-methyl-3-(5-methyl-1H-imidazol-4-yl)-1-(1-methyl-1H-indol-3-yl)-1-propanone;
3-(5-methyl-1H-imidazol-4-yl)-1-(1,2-dimethyl-1H-indol-3-yl)-1-propanone;
1-(1-methyl-1H-indol-3-yl)-3-(5-propyl-1H-imidazol-4-yl)-1-propanone;
2,2-dimethyl-3-(5-methyl-1H-imidazol-4-yl)-1-(1-methyl-1H-indol-3-yl)-1-propanone;
3-(5-methyl-1H-imidazol-4-yl)-1-(1,7-dimethyl-1H-indol-3-yl) propanone
and their physiologically acceptable salts and solvates.

Suitable physiologically acceptable salts of the indoles of general formula (I) include acid addition salts formed with organic or inorganic acids for example, hydrochlorides, hydrobromides, sulphates, phosphates, citrates, succinates, tartrates, fumarates and maleates. The solvates may, for example, be hydrates.

It will be appreciated that the invention extends to other physiologically acceptable equivalents of the compounds according to the invention, i.e. physiologically acceptale compounds which are converted in vivo into the parent compound of formula (I).

Compounds of the invention are potent and selective antagonists of 5-HT-induced depolarisation of the rat isolated vagus nerve preparation and thus act as potent and selective antagonists of the 'neuronal' 5-HT receptor type located on primary afferent nerves. Receptors of this type are now designated as $5\text{-HT}_3$ receptors. Such receptors are also believed to be present in the central nervous system. 5-HT occurs widely in the neuronal pathways in the central nervous system and disturbance of these 5-HT containing pathways is known to alter aspects of behaviour such as mood, psychomotor activity, appetite and memory.

Compounds of formula (I), which antagonise the effect of 5-HT at $5\text{-HT}_3$ receptors, are useful in the treatment of conditions such as psychotic disorders (e.g. schizophrenia and mania); anxiety; and nausea and vomiting. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain.

Compounds of formula (I) may also be used in the treatment of dependency on drugs and substances of abuse, depression, and dementia and other cognitive disorders.

Unlike existing drug treatments for these conditions, the compounds of the invention, because of their high selectivity for $5\text{-HT}_3$ receptors, would not be expected to produce undesirable side effects. Thus, for example, neuroleptic drugs may exhibit extrapyramidal effects, such as tardive dyskinesia, and benzodiazepines may cause dependence.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndriome; migraine; or pain, which comprises administering an effective amount of a compound of formula (I) or a physiologically acceptable salt or solvate thereof.

Accordingly, the invention also provides a pharmaceutical composition which comprises at least one compound selected from indole derivatives of the general formula (I), and their physiologically acceptable salts and solvates e.g. hydrates, adapted for use in human or veterinary medicine, and formulated for administration by any convenient route.

Such compositions may be formulated in conventional manner using one or more physiologically acceptable carriers or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by injection. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurized packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonsists (e.g. ranitidine, sufotidine or loxtidine) or $H+K+ATPase$ inhibitors (e.g. omeprazole).

A proposed dose of the compounds of the invention for administration to man (of approximately 70 kg body weight) is 0.001 to 100 mg, preferably 0.01 to 50 mg of the active ingredient per unit dose which could be administered, for example, 1 to 4 times per day. It will be appreciated that it may be necesssary to make routine variations to the dosage, depending on the age and condition of the patient. The dosage will also depend on the route of administration.

According to another aspect of the invention, compounds of general formula (I) and physiologically acceptable salts or solvates or physiologically acceptable equivalents thereof may be prepared by the general methods outlined hereinafter. In the following description, the groups $R^1$ to $R^4$, A, B and Im are as defined for compounds of general formula (I) unless otherwise stated.

According to a first general process (A), a compound of general formula (I), wherein A-B represents the group $R^3R^4C—CH_2$, or a physiologically acceptable salt or solvate thereof, may be prepared by reacting a compound of formula (II):

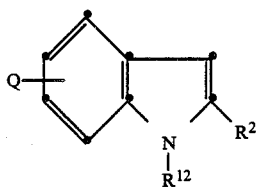

(II)

(wherein $R^{12}$ represents a group $R^1$ as previously defined or a group MgHal, where Hal is halide ion (eg a bromide or iodide ion) or a protected derivative thereof (eg an N-phenylsulphonyl derivative), with an acylating reagent derived from an acid of general formula (III):

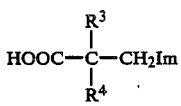

(III)

or a salt or protected derivative, thereof, followed where necessary by removal of any protecting groups.

Suitable acylating reagents include acid halides (e.g. acid chlorides), anhydrides (e.g. symmetrical anhydrides or mixed anhydrides formed for example with pivaloyl chloride), amides, and nitriles.

When the group $R^{12}$ represents $R^1$, an indole of formula (II) may be condensed with an acid halide (e.g. an acid chloride) or an anhydride (e.g. pivalic anhydride) derivative of the acid (III) under Friedel-Crafts conditions. In this particular embodiment of general process (A), $R^1$ preferably represents an acyl group. Thus, the reaction is desirably conducted in the presence of a Lewis acid, such as stannic chloride or aluminium chloride. The reaction may conveniently be effected in an organic solvent such as a halogenated hydrocarbon (e.g. dichloromethane or dichloroethane) or carbon disulphide, and at a temperature in the range $-5°$ to $+85°$ C.

When employing an indole of formula (II) in which $R^{12}$ represents MgHal, the acylation reaction with an acid halide or anhydride may be effected in a non-polar organic solvent such as an ether (e.g. diethyl ether) or an aromatic hydrocarbon (e.g. toluene) or mixtures thereof, at a temperature in the range $-5°$ to $+80°$ C.

Indoles of formula (II) may also be acylated according to the Vilsmeier-Haack reaction, using a tertiary amide derivative of an acid of formula (III), such as the corresponding N,N-dimethylpropanamide compound in the presence of a phosphoryl halide such as phosphorus oxychloride. This reaction may be effected in the presence or absence of a solvent. Solvents which may conveniently be employed include halogenated hydrocarbons such as 1,2-dichloroethane. The reaction temperature may be in the range 20° to 100° C. In this embodiment of general process (A), $R^{12}$ is preferably a group $R^1$.

Indoles of formula (I) wherein $R^2$ is other than hydrogen may be prepared according to general process (A) by reaction with a nitrile corresponding to the acid of formula (III), in the presence of hydrogen chloride. If an indole of formula (II) in which $R^{12}$ represents MgHal is employed, this may first be reacted with the nitrile to form an imine, which may subsequently be converted into the corresponding ketone by hydrolysis with an acid.

Acylating reagents corresponding to the acids of formula (III) may be prepared by conventional methods. Thus, an acid halide may be prepared by reacting an acid (III) or a salt thereof with a halogenating agent (e.g. thionyl chloride or phosphorus pentachloride).

Anhydrides may be prepared by reacting an acid (III) with an appropriate acid halide in the presence of a base, or alternatively by reacting an acid halide corresponding to the compound of formula (III) with an acid, in the presence of a base.

An amide may be prepared by reaction of the corresponding acid chloride with the appropriate amine (e.g. dimethylamine). Alternatively an amide corresponding to an acid (III) may be prepared by catalytic hydrogenation of the corresponding propenamide compound, which may itself be obtained from the appropriate propenoic acid via an acid halide derivative.

A nitrile corresponding to an acid of formula (III) may be prepared by dehydration of the corresponding unsubstituted amide derivative, using a conventional dehydrating agent such as phosphorus pentoxide, phosphorus oxychloride or phosphorus pentachloride.

Acids of general formula (III) may themselves be prepared for example from the corresponding esters by acid- or base-catalysed hydrolysis.

The esters may be prepared for example by reacting an aldehyde of formula (IV):

 (IV)

or a protected derivative thereof with a phosphonate of formula (V):

 (V)

wherein R¹³ represents a group such as an alkyl (e.g. methyl or ethyl), aryl (e.g. phenyl) or aralkyl (e.g. benzyl) group and R¹⁴ represents an alkyl (e.g. ethyl) or aryl (e.g. phenyl) group, which has been pre-treated with a base such as an alkali metal hydride (eg sodium hydride) in an inert organic solvent such as an ether (eg tetrahydrofuran) or a substituted amide (eg dimethylformamide), to give a compound of formula (VI):

(VI)

followed by catalytic hydrogenation of the double bond, using for example palladium on charcoal as the catalyst. Where it is desired to produce an ester corresponding to the acid (III) in which $R^3$ and $R^4$ both represent alkyl groups, the hydrogenation may be followed by alkylation to introduce the desired $R^4$ group and where appropriate, $R^3$.

Compounds of formula (IV) can be prepared, for example, by oxidation of the corresponding methanol-substituted imidazole compound, or a protected derivative thereof, with an oxidising agent such as manganese dioxide.

According to another general process (B) a compound of general formula (I), wherein A-B represents the group $R^3C\!=\!CH$, or a physiologically acceptable salt or solvate thereof, may be prepared by condensing a compound of formula (VII):

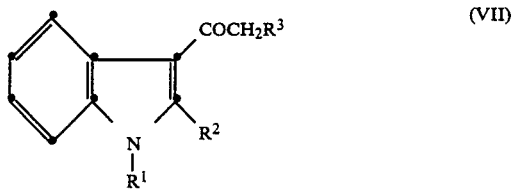
(VII)

wherein $R^1$ is as defined in formula (Ia), or a protected derivative thereof, with a compound of formula (IV), or a protected derivative thereof, in the presence of a base, followed where necessary by removal of any protecting groups. The reaction may conveniently be effected using an alkali metal hydroxide (eg sodium or potassium hydroxide) in an alcohol (eg ethanol or t-butanol) or water, or mixtures thereof, or using an alkali metal alkoxide (eg sodium ethoxide or potassium t-butoxide) in the corresponding alcohol (eg ethanol or t-butanol) or in an inert solvent such as an ether (eg tetrahydrofuran), and at a temperature of 0° to 100° C.

Compounds of formula (VII) may be prepared by treating an indole of formula (II) (wherein R¹² represents a group R¹ as defined in formula (1a)) with an acylating derivative of an acid of formula (VIII):

under conditions analogous to those described for process (A) above.

According to another general process (C), a compound of general formula (I), or a salt or protected derivative thereof, may be converted into another compound of formula (I) using conventional techniques. Such conventional techniques include hydrogenation, alkylation, acylation and sulphonylation, and acid-catalysed cleavage using protection and deprotection where necessary.

Thus, for example, compounds of formula (Ia) in which A-B represents the group $R^3CH\!-\!CH_2$ may be prepared by hydrogenating the corresponding compounds of formula (Ia) in which A-B represents the group $R^3C\!=\!CH$. Hydrogenation may also be used to convert an alkenyl or an alkynyl substituent into an alkyl substituent, or an alkynyl into an alkenyl substituent.

Hydrogenation according to general process (C) may be effected using conventional procedures, for example using hydrogen in the presence of a noble metal catalyst (e.g. palladium, Raney nickel, platinum or rhodium). The catalyst may be supported on, for example, charcoal, or alternatively a homogeneous catalyst such as tris(triphenylphosphine)rhodium chloride may be used. The hydrogenation will generally be effected in a solvent such as an alcohol (e.g. ethanol), an ether (e.g. dioxan), or an ester (e.g. ethyl acetate), and at a temperature in the range −20° to +100° C., preferably 0° to 50° C.

Alkylation according to general process (C) may be effected for example on a compound of formula (I) where one or more of $R^1$, $R^3$, $R^4$, $R^5$, $R^6$, $R^{10}$ and $R^{11}$ represent a hydrogen atom or Q represents a hydroxyl group.

The term 'alkylation' also includes the introduction of other groups such as cycloalkyl or alkenyl groups. Thus, for example, a compound of formula (I) in which $R^1$ represents a hydrogen atom may be converted into the corresponding compound in which $R^1$ represents a $C_{1-6}$ alkyl, $C_{3-7}$ cycloalkyl, $C_{3-6}$ alkenyl, $C_{3-10}$ alkynyl, $C_{3-7}$cycloalkyl$C_{1-4}$alkyl or phenyl$C_{1-3}$alkyl group, or a compound in which at least one of $R^3$ and $R^4$ represents a hydrogen atom may have the hydrogen atom(s) replaced by a $C_{1-6}$ alkyl group. Similarly, compounds of formula (I) in which $R^6$ represents a hydrogen atom may be 'alkylated' to give compounds of formula (I) in which $R^6$ represents a $C_{1-6}$ alkyl, $C_{3-7}$cycloalkyl, $C_{3-6}$ alkenyl or phenyl $C_{1-3}$ alkyl group.

The above alkylation reactions may be effected using the appropriate alkylating agent selected from compounds of formula $R^{15}Z$ where $R^{15}$ represents a $C_{1-6}$ alkyl, $C_{3-7}$ cycloalkyl, $C_{3-6}$ alkenyl, $C_{3-10}$ alkynyl, $C_{3-7}$ cycloalkyl$C_{1-4}$alkyl or phenyl$C_{1-3}$alkyl group, and Z represents a leaving atom or group such as a halogen atom (e.g. chlorine or bromine), or an acyloxy group (e.g. acetoxy, trifluoromethanesulphonyloxy, p-toluenesulphonyloxy or methanesulphonyloxy); or a sulphate of formula $(R^{15})_2SO_4$.

The alkylation reaction is conveniently carried out in an inert organic solvent such as a substituted amide (eg dimethylformamide), an ether (eg tetrahydrofuran) or an aromatic hydrocarbon (eg toluene), preferably in the presence of a base. Suitable bases include, for example, alkali metal hydrides (eg sodium hydride), alkali metal amides (eg sodium amide or lithium diisopropylamide), alkali metal carbonates (eg sodium carbonate) or an alkali metal alkoxide (eg sodium or potassium methoxide, ethoxide or t-butoxide). The reaction may conveniently be effected a temperature in the range −70° to +100° C., preferably 0° to 50° C.

Acylation and sulphonylation according to general process (C) may be used to prepare a compound of formula (I) wherein $R^1$ represents the group —$CO_2R^8$, —$COR^8$, —$COR^8R^9$ or —$SO_2R^8$ from the corresponding compound of formula (I) wherein $R^1$ represents a hydrogen atom, or a protected derivative thereof, followed where necessary by removal of any protecting groups. The acylation/sulphonylation reaction may be effected using an appropriate acylating/sulphonylating agent according to conventional procedures.

Suitable acrylating agents include acyl halides (e.g. an acyl chloride, bromide or iodide), mixed and symmetrical anhydrides (e.g. a symmetrical anhydride of formula $(R^8CO)_2O$), lower alkyl haloformates (e.g. lower alkyl chloroformates), carbamoyl halides (e.g. carbamoyl chlorides of formula $R^8R^9NCOCl$), carbonates and isocyanates (e.g. isocyanates of formula $R^8NCO$). Suitable sulphonylating agents include sulphonyl halides (e.g. an alkylsulphonyl or arylsulphonyl chloride, bromide or iodide) and sulphonates (e.g. hydrocarbylsulphonates such as p-toluenesulphonate).

The reaction may conveniently be effected in the presence of a base such as an alkali metal hydride (e.g. sodium or potassium hydride), an alkali metal carbonate (e.g. sodium or potassium carbonate), an alkali metal alkoxide (e.g. potassium t-butoxide), butyllithium, lithium diisopropylamide or an organic tertiary amine (e.g. triethylamine or pyridine).

Suitable solvents which may be employed in the acylation/sulphonylation of general process (C) include substituted amides (e.g. dimethylformamide or dimethylacetamide), ethers (e.g. tetrahydrofuran or dioxan), halogenated hydrocarbons (e.g. methylene chloride), nitriles (e.g. acetonitrile) and esters (e.g. ethyl acetate). The reaction may conveniently be effected at a temperature of from $-10°$ to $+150°$.

Acid-catalysed cleavage according to general process (C) may be used to prepare a compound of formula (I) in which Q represents a hydroxyl group from the corresponding compound in which Q represents an alkoxy or benzyloxy group by acid-catalysed cleavage. The reaction may be effected using a Lewis acid such as boron tribromide or aluminium trichloride, in a solvent such as a halogenated hydrocarbon (e.g. dichloromethane). The reaction temperature may conveniently be in the range $-80°$ to $+100°$ C.

According to another general process (D), a compound of general formula (Ia) wherein A-B represents the group $R^3R^4C$—$CH_2$, or a physiologically acceptable salt or solvate thereof, may be prepared by oxidising a compound of formula (IX):

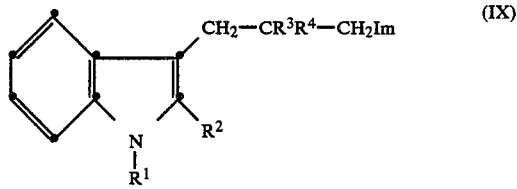

wherein $R^1$ is as defined in formula (Ia), or a protected derivative thereof, followed where necessary by removal of any protecting groups. The oxidation process may be effected using conventional methods and the reagents and reaction conditions should be chosen such that they do not cause oxidation of the indole group. Thus, the oxidation process is preferably effected using a mild oxidising agent.

Suitable oxidising agents include quinones in the presence of water (eg 2,3-dichloro-5,6-dicyano-1,4-benzoquinone or 2,3,5,6-tetrachloro-1,4-benzoquinone), selenium dioxide, a cerium (IV) oxidising agent (eg ceric ammonium nitrate), a chromium (VI) oxidising agent (eg a solution of chromic acid in acetone, for example Jones' reagent) or chromium trioxide in pyridine.

Suitable solvents may be selected from ketones (eg acetone or butanone), ethers (eg tetrahydrofuran or dioxan), amides (eg dimethylformamide), alcohols (eg methanol), hydrocarbons (eg toluene), halogenated hydrocarbons (eg dichloromethane) and water or mixtures thereof.

The process is conveniently effected at a temperature of $-70°$ to $+50°$ C. It will be understood that the choice of oxidising agent will effect the preferred reaction temperature and solvent.

Compounds of formula (IX) may be prepared by reduction of a compound of formula (I), or a protected derivative thereof, using a suitable reducing agent. Suitable reducing agents include diisobutylaluminium hydride, in a suitable solvent such as an ether (eg tetrahydrofuran), a hydrocarbon (eg hexane or toluene) or a halogenated hydrocarbon (eg dichloromethane) at a temperature of $-80°$ to $+25°$ C., and lithium aluminium hydride in a suitable solvent such as an ether (eg tetrahydrofuran or ether) at a temperature of $-20°$ to $+50°$ C.

According to another general process (E), a compound of general formula (Ia), wherein A-B represents the group $R^3R^4C$—$CH_2$, or a physiologically acceptable salt or solvate thereof, may be prepared by reacting a compound of formula (X):

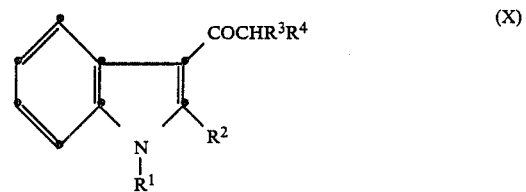

wherein $R^1$ is as defined in formula (Ia), or a protected derivative thereof, with a compound of formula (XI):

wherein L represents a leaving atom or group, such as halogen atom (eg chlorine or bromine), or an acyloxy group (eg acetoxy, trifluoromethanesulphonyloxy, p-toluenesulphonyloxy or methanesulphonyloxy), or a protected derivative thereof, in the presence of a base, followed where necessary by removal of any protecting groups.

Suitable bases include alkali metal hydrides (eg sodium or potassium hydride), alkali metal alkoxides (eg potassium-t-butoxide) or lithium diisopropylamide. The reaction may conveniently be carried out in an inert solvent such as an ether (eg tetrahydrofuran), a substituted amide (eg dimethylformamide), or an aromatic hydrocarbon (eg toluene) and at a temperature of $-70°$ to $+50°$ C.

It should be appreciated that in the above transformations it may be necessary or desirable to protect any sensitive groups in the molecule of the compound in question to avoid undesirable side reactions. For example, it may be necessary to protect the keto group, for example, as a ketal or a thioketal. It may also be necessary to protect the indole and/or imidazole nitrogen atoms, for example with an arylmethyl (e.g. benzyl or trityl), alkyl (e.g. t-butyl), alkoxymethyl (e.g. methoxymethyl), acyl (eg benzyloxycarbonyl) or a sulphonyl (eg N,N-dimethylaminosulphonyl or p-toluenesulphonyl) group.

When Q represents a hydroxyl group it may be necessary to protect the hydroxyl group, for example with an arylmethyl (e.g. benzyl or trityl) group.

Thus according to another general process (F), a compound of formula (I) may be prepared by the removal of any protecting groups from a protected form of a compound of formula (I). Deprotection may be effected using conventional techniques such as those described in 'Protective Groups in Organic Synthesis' by Theodora W. Greene (John Wiley and Sons, 1981).

For example a ketal such as an alkyleneketal group may be removed by treatment with a mineral acid such as hydrochloric acid. A thioketal group may be cleaved by treatment with a mercuric salt, (e.g. mercuric chloride), in a suitable solvent, such as ethanol. An arylmethyl N-protecting group may be cleaved by hydrogenolysis in the presence of a catalyst (e.g. palladium on charcoal) and a trityl group may also be cleaved by acid hydrolysis (e.g. using dilute hydrochloric or acetic acid). An alkoxyalkyl group may be removed using a Lewis acid such as boron tribromide. An acyl group may be removed by hydrogenation (eg with sodium in liquid ammonia) or under acidic conditions (eg using hydrogen bromide or trifluoroacetic acid). A sulphonyl group may be removed by alkaline hydrolysis.

An arylmethyl OH-protecting group may be cleaved under acidic conditions (e.g. with dilute acetic acid, hydrobromic acid or boron tribromide) or by hydrogenolysis in the presence of a catalyst (e.g. palladium on charcoal).

Where it is desired to isolate a compound of the invention as a salt, for example a physiologically acceptable salt, this may be achieved by treating the free base of general formula (I) with an appropriate acid, preferably with an equivalent amount, in a suitable solvent such as an alcohol (e.g. ethanol or methanol), an ester (eg ethyl acetate) or an ether (eg tetrahydrofuran).

Physiologically acceptable equivalents of a compound of formula (I) may be prepared according to conventional methods. Thus, for example, an N-acyl derivative may be prepared using conventional acylation techniques.

Individual enantiomers of the compounds of the invention may be obtained by resolution of a mixture of enantiomers (e.g a racemic mixture) using conventional means, such as an optically active resolving acid; see for example 'Stereochemistry of Carbon Compounds' by E. L. Eliel (McGraw Hill 1962) and 'Tables of Resolving Agents' by S. H. Wilen.

The methods indicated above for preparing the compounds of the invention can be used as the last main step in the preparative sequence. The same general methods can be used for the introduction of the desired groups at an intermediate stage in the stepwise formation of the required compound, and it will be appreciated that these general methods can be combined in different ways in such multi-stage processes. The sequence of the reactions in multi-stage processes should of course the chosen so that the reaction conditions used do not affect groups in the molecule which are desired in the final product.

The invention is further illustrated by the following Examples. All temperatures are in °C. Thin layer chromatography (t.l.c.) was carried out over silica, and flash column chromatography (FCC) and short-path column chromatography (SPCC) on silica (Merck 9385 and Merck 7747 respectively). Solvent System A as used for chromatography denotes dichloromethane:ethanol:0.88 ammonia solution. Organic extracts were dried over sodium sulphate or magnesium sulphate. The following abbreviations are used: DMF-dimethylformamide, THF-tetrahydrofuran, IMS-industrial methylated spirits.

INTERMEDIATE 1

(E)-N,N-Dimethyl-3-(1H-imidazol-4-yl)-2-propenamide

A mixture of urocanic acid (1.38 g) and phosphate pentachloride (2.08 g) was heated under nitrogen at 100°–110° for 1.5 h, then at 190° for 1 h. The mixture was cooled, washed twice with dichloromethane (50 ml) and filtered. The solid was treated with a solution of dimethylamine in I.M.S. (33% w/v; 50 ml) and stirred at room temperature for 2 h. The mixture was evaporated in vacuo, dissolved in ethanol (25 ml) and purified by FCC, eluting with System A (89:10:1), to give a gum. This was triturated with dry ether (30 ml), to give the title compound (0.95 g) as a solid, m.p. 142°–144° (decomp.).

INTERMEDIATE 2

N,N-Dimethyl-3-(1H-imidazol-4-yl)-1-propanamide hydrochloride

A suspension of 10% palladium oxide on carbon (0.18 g) in ethanol (20 ml) was stirred under hydrogen for 30 min. A solution of (E)-N,N-dimethyl-3-(1H-imidazol-4-yl)-2-propenamide (1.0g) in ethanol (40 ml) was added and stirring was continued overnight (18 h). The suspension was filtered through Hyflo and evaporated in vacuo to give an oil (1.12 g), which was dissolved in ethanol (15 ml) and acidified with ethereal hydrogen chloride. The resulting precipitate was filtered off, washed with dry ether (ca. 100 ml) and dried (20 mmHg, 100°, 3 h) to give the crystalline title compound (1.11 g), m.p. 171°–173°.

INTERMEDIATE 3

5-Methyl-1-(triphenylmethyl)-1H-imidazole-4-methanol

A solution of triphenylchloromethane (13.1 g) in dry DMF (80 ml) was added dropwise over 0.5 h to a stirred solution of 4-methyl-5-imidazolemethanol hydrochloride (7.0 g) and triethylamine (9.52 g) in dry DMF (75 ml) at room temperature under nitrogen, and stirring was continued for 2.5 h. The suspension was poured onto ice (600 ml), stirred for 0.5 h and filtered to give a solid (12.0 g). This solid was triturated twice with acetone (2×250 ml) to give the title compound (8.4 g) as a white solid, t.l.c. (System A 94.5:5:0.5), Rf 0.19.

INTERMEDIATE 4

5-Methyl-1-(triphenylmethyl)-1H-imidazole-4-carboxaldehyde

A mixture of 5-methyl-1-(triphenylmethyl)-1H-imidazole-4-methanol (4.0 g), manganese dioxide (activated) (40 g) and dioxan (225 ml) was stirred at room temperature overnight. The suspension was filtered through Hyflo, the solid washed with hot chloroform (1 l) and the combined filtrates evaporated in vacuo to leave an off-white solid (4.0 g). This solid was purified by FCC eluting with chloroform to give an off-white solid which was triturated with hexane (ca. 50 ml) to give the title compound (2.99 g) as a white crystalline solid, m.p. 184°–188° (decomp.).

INTERMEDIATE 5

(E)-N,N-Dimethyl-3-[5-methyl-1-(triphenylmethyl)-1H-imidazol-4-yl]-2-propenamide A solution of dimethyl[2-(dimethylamino)-2-oxoethyl]phosphonate (4.88 g) in dry THF (25 ml) was added dropwise with stirring to a suspension of sodium hydride (1.54 g of a 78% dispersion in oil pre-washed with hexane (2×40 ml)) in dry THF (25 ml) under nitrogen at −10°. The suspension was stirred at room temperature for 1 h, cooled to −10° and 5-methyl-1-(triphenylmethyl)-1H-imidazole-4-carboxaldehyde (6.51 g) in dry THF (50 ml) was added. The mixture was stirred at room temperature for 64 h, poured into 8% aqueous sodium bicarbonate (20 ml) and extracted with ethyl acetate (3×200 ml). The combined, dried organic extracts were evaporated to give a yellow semisolid (8.0 g). This was purified by FCC eluting with dichloromethane:ethanol (95:5) to give on trituration with hexane the title compound (6.4 g) as a white solid, m.p. 195°–197°.

INTERMEDIATE 6

N,N-Dimethyl-3-(5-methyl-1H-imidazol-4-yl)propanamide

A solution of (E)-N,N-dimethyl-3-[5-methyl-1-(triphenylmethyl)-1H-imdiazol-4-yl]-2-propenamide (6.1 g) in absolute ethanol (100 ml) was added to a suspension of pre-reduced 10% palladium oxide on charcoal (2.0 g) in absolute ethanol (50 ml). The mixture was stirred in a hydrogen atmosphere for 72 h then filtered (Hyflo) and evaporated to give a grey oily solid (ca. 6 g). Column chromatography on silica gel (Merck 7734), made up in EtOAc:MeOH:Et₃N (80:19:1) eluting with ethyl acetate:methanol (4:1) gave the title compound (2.52 g) as a white solid, m.p. 62°–64°.

INTERMEDIATE 7

N,N-Dimethyl-3-(5-methyl-1H-imidazol-4-yl)propanamide dihydrochloride

A solution of (E)-N,N-dimethyl-3-[5-methyl-1-(triphenylmethyl)-1H-imidazol-4-yl]-2-propenamide (6.0 g) in ethanol (100 ml) was hydrogenated at room temperature and pressure over 10% palladium oxide on carbon (dry, 2.0 g, pre-reduced in ethanol (25 ml)) for 48 h. The catalyst was filtered off (Hyflo), replaced with fresh palladium oxide (2.0 g) and hydrogenation continued for 72 h. The catalyst was filtered off (Hyflo) and the filtrate evaporated in vacuo to yield a yellow oil. This was dissolved in ethanol (15 ml) and acidified with ethanolic hydrogen chloride (to pH1). Dry ether (500 ml) was added and the resulting precipitate was filtered off to give the title compound (1.72 g) as a white powder, m.p. 142°–144°.

INTERMEDIATE 8

4-Iodo-2-methyl-1-(4-methylbenzenesulphonyl)-1H-imidazole

Sodium hydrogen carbonate (9 g) was added to a stirred solution of 4-iodo-2-methyl-1H-imidazole (9.0 g) in acetonitrile (125 ml) followed by a solution of p-toluenesulphonyl chloride (8.3 g) in acetonitrile (50 ml). The resulting mixture was maintained at ca. 40° for 5 h. The reaction mixture was filtered, concentrated in vacuo to ca. 30 ml and n-hexane (ca. 350 ml) was added, precipitating the title compound (7.8 g) as crystals, m.p. 113°–114°. Concentration of the mother liquors (to ca. 50 ml) afforded further title compound (6.1 g), m.p. 112°–114°.

INTERMEDIATE 9

(E)-N,N-Dimethyl-3-[2-methyl-1-(4-methylbenzenesulphonyl)-1H-imidazol-4-yl]-2-propenamide A mixture of 4-iodo-2-methyl-1-(4-methylbenzenesulphonyl)-1H-imidazole (3.62 g), N,N-dimethylacrylamide (1.05 g), palladium (II) acetate (125 mg) and triethylamine (2 ml) in acetonitrile (3 ml) was heated at 120° under nitrogen for 2.5 h. The cooled mixture waspartitioned between chloroform (3×50 ml) and 2N sodium carbonate (75 ml), and the combined organic layers were dried and evaporated in vacuo to leave a solid (ca. 3.0 g). This solid was purified by FCC eluting with chloroform to give the crystalline title compound (1.55 g), m.p. 162°–163°.

INTERMEDIATE 10

(E)-N,N-Dimethyl-3-(2-methyl-1H-imidazol-4-yl)-2-propenamide

A solution of (E)-N,N-dimethyl-3-[2-methyl-1-(4-methylbenzenesulphonyl)-1H-imidazol-4-yl]-2-propenamide (1.0 g) in pyridine (5 ml) and acetic anhydride (10 ml) was stirred at room temperature for 16 h. The reaction mixture was evaporated in vacuo, methanol (15 ml) was added and stirring was continued for 1 h. The mixture was evaporated in vacuo and the resulting gum partitioned between potassium carbonate solution (ca. 25% saturated) (30 ml) and chloroform (4×25 ml). The combined organic layers were dried, evaporated in vacuo and the residue triturated with ether (30 ml) to give the title compound (340 mg) as a solid, t.l.c. (ether:methanol 9:1), Rf 0.07.

INTERMEDIATE 11

N,N-Dimethyl-3-(2-methyl-1H-imidazol-4-yl)propanamide hydrochloride

A solution of (E)-N,N-dimethyl-3-(2-methyl-1H-imidazol-4-yl)-2-propenamide (340 mg) in methanol (10 ml) and HCl-saturated ethanol (2 ml) was added to a previously hydrogen-saturated suspension of 10% palladium on charcoal (50% paste with water) (35 mg) in methanol (10 ml) and the resulting suspension stirred at room temperature under hydrogen for 4 h. The mixture was filtered, concentrated in vacuo to ca. 5 ml and ethyl acetate (ca. 40 ml) was added, precipitating the title compound (275 mg) as white flakes, t.l.c. (System A 89:10:1), Rf 0.14. Addition of further ethyl acetate (40 ml) to the mother liquors precipitated further title compound (31 mg).

INTERMEDIATE 12

Ethyl 2-chloro-3-oxohexanoate

Sulphuryl chloride (175 ml) was added to a rapidly stirred and cooled solution of ethyl 3-oxohexanoate (300 ml) in chloroform (150 ml) whilst maintaining the temperature at 10°–15°. The mixture was stirred overnight at room temperature, then heated under reflux for 0.5 h. The cooled reaction mixture was washed with water (0.5 l), 2N sodium bicarbonate (0.5 l) and water (0.5 l), dried and concentrated in vacuo. Fractionation gave the title compound (341.8 g) as a pale yellow liquid b.p. 106°–108°/ca. 10 mmHg, t.l.c. (ether:hexane 1:1), Rf 0.60.

INTERMEDIATE 13

Ethyl 5-propyl-1H-imidazole-4-carboxylate

A mixture of formamide (98%, 140 ml), ethyl 2-chloro-3-oxohexanoate (60.0 g) and water (12.5 ml) was heated at reflux under nitrogen for 3 h, cooled and partitioned between 1N hydrochloric acid (500 ml) and ether (3×200 ml). The acidic aqueous layer was basified with 5N sodium hydroxide (to pH8), the brown precipitate was collected by filtration and dried (vac. oven, 90°, 2 h), to give the title compound (23.3 g) as a brown solid, m.p. 175°–179°.

INTERMEDIATE 14

5-Propyl-1H-imidazole-4-methanol hydrochloride

A suspension of ethyl 5-propyl-1H-imidazole-4-carboxylate (5.00 g) in dry THF (250 ml) was added to a stirred suspension of lithium aluminium hydride (1.50 g) in dry THF (100 ml) over 5 min under nitrogen. The mixture was then heated under reflux for 1 h, cooled to 35° and treated sequentially with water (1.5 ml), 15% w/v sodium hydroxide solution (4.5 ml) and water (2.0 ml). The mixture was filtered and evaporated in vacuo to leave an orange oil (ca. 4.3 g). This oil was dissolved in absolute alcohol (5 ml) and dry ether (200 ml), and ethereal hydrogen chloride was added until the solution was just acidic (pH1). The mixture was evaporated in vacuo, further dry ether (150 ml) was added, precipitating the title compound (3.70 g) as a brown solid, m.p. 149°–152°.

INTERMEDIATE 15

5-Propyl-1H-imidazole-4-carboxaldehyde

A mixture of 5-propyl-1H-imidazole-4-methanol (4.0 g) and manganese (IV) oxide (10.0 g) in 1,4-dioxan (150 ml) was heated at reflux under nitrogen for 1 h. The hot suspension was filtered (Hyflo), washed with hot 1,4-dioxan (100 ml) and evaporated to give the title compound (2.9 g) as a solid, m.p. 120°–124°.

INTERMEDIATE 16

(E)-N,N-Dimethyl-3-(5-propyl-1H-imidazol-4-yl)-2-propenamide

A solution of dimethyl [2-(dimethylamino)-2-oxoethyl]phosphonate (1.91 g) in dry THF (5 ml) was added dropwise under nitrogen to a cold (−10°) suspension of sodium hydride (0.64 g, 73% dispersion in oil) in dry THF (5 ml). After stirring at room temperature for 1 h, a solution of 5-propyl-1H-imidazole-4-carboxaldehyde (1.0 g) in dry THF (10 ml) was added at −10° and the mixture allowed to stir at room temperature for a further 18 h then at reflux for 6 h. The solution was poured into 8% sodium bicarbonate solution (50 ml) and extracted with dichloromethane (3×25 ml). The combined extracts were dried, filtered and evaporated to give an oil (1.9 g). Column chromatography on silica gel (Merck 7734) eluting with ethyl acetate:methanol (17:3) gave a yellow oil (0.82 g). The material ws dissolved in 2N hydrochloric acid (20 ml) and washed with ethyl acetate (2×15 ml). The aqueous layer was basified (to pH~9) with sodium bicarbonate and extracted with dichloromethane (2×20 ml). The combined extracts were dried, filtered and evaporated to give the title compound (0.61 g) as a viscous yellow oil, t.l.c. (ethyl acetate:methanol 17:3), Rf 0.35.

INTERMEDIATE 17

N,N-Dimethyl-3-(5-propyl-1H-imidazol-4-yl)propanamide

A solution of (E)-N,N-dimethyl-3-(5-propyl-1H-imidazol-4-yl)-2-propenamide (500 mg) in ethanol (25 ml) was added to a suspension of pre-reduced 10% palladium oxide on carbon catalyst (150 mg, 50% paste with water) in ethanol (15 ml). The mixture was stirred in a hydrogen atmosphere for 2 h, then filtered (Hyflo) and evaporated to give the title compound (500 mg) as a colorless oil, t.l.c. on Et$_3$N impregnated SiO$_2$ (ethyl acetate:methanol 4:1), Rf 0.33.

INTERMEDIATE 18

(E)-3-[5-Methyl-1-(triphenylmethyl)-1H-imidazol-4-yl]-1-(1H-indol-3-yl)-2-propen-1-one A mixture of 5-methyl-1-(triphenylmethyl)-1H-imidazol-4-carboxaldehyde (4.90 g), 3-acetylindole (2.24 g) and potassium hydroxide (6.08 g) in absolute ethanol (100 ml) and water (50 ml) was heated at 80° for 24 h. The suspension was poured into 2N sodium carbonate solution (300 ml) and extracted with dichloromethane (3×150 ml). The combined extracts were dried, filtered and evaporated to give an orange solid (6.5 g) which was triturated with ethyl acetate (50 ml) to give the title compound (2.42 g) as a yellow solid, m.p. 240°–242°.

INTERMEDIATE 19

3-[5-Methyl-1-(triphenylmethyl)-1H-imidazol-4-yl]-1-(1H-indol-3-yl)-1-propanone

A suspension of (E)-3-[5-methyl-1-(triphenylmethyl-1H-imidazol-4-yl]-1-(1H-indol-3-yl)-2-propen-1-one (500 mg) in ethanol (25 ml) was added to a suspension of pre-reduced 10% palladium oxide on charcoal catalyst (50 mg; 50% paste with water) in ethanol (10 ml). The mixture was hydrogenated for 120 h then filtered through Hyflo and evaporated give a white solid (265 mg). The Hyflo and catalyst residue was stirred with dichloromethane:ethanol (1:1, ca. 200 ml) for 2 h, filtered and evaporated to give an off-white solid (ca. 240 mg). The two products were combined and purified by FCC eluting with System A (200:10:1) to give the title compound (405 mg) as a white solid, m.p. 225°–227°.

INTERMEDIATE 20

1-(1-Methyl-1H-indol-3-yl)-3-[5-methyl-1-(triphenylmethyl)-1H-imidazol-4-yl]-1-propanone A suspension of Intermediate 19 (0.5 g) in dry DMF (3 ml) was added dropwise to a stirred suspension of sodium hydride (40 mg, 73% in oil) in dry DMF (1 ml) under nitrogen. The resulting mixture was stirred at 20° for 0.75 h and treated with iodomethane (0.062 ml) at 20° for 2.5 h. The resulting yellow solution was poured into water (100 ml) to precipitate the title compound (0.5 g) as a solid, t.l.c. (System A 100:8:1), Rf 0.19.

INTERMEDIATE 21

2-Methyl-1-(1-methyl-1H-indol-3-yl)-3-[5-methyl-1-(triphenylmethyl)-1H-imidazol-4-yl]-1-propanone Lithium diisopropylamine mono(tetrahydrofuran) (1.5M in cyclohexane, 11.5 ml) was added dropwise to a cold (−70°) solution of 1-(1-methyl-1H-indol-3-yl)-3-[5-methyl-1-(triphenylmethyl)-1H-imidazol-4-yl]-1-propanone (8.8 g) in dry THF (175 ml) under nitrogen. The stirred solution was allowed to warm to 20° over 1 h then cooled to −70°. Iodomethane (2.15 ml) was added and the mixture was allowed to reach 20° over 1 h and stirred for a further 2 h. More iodomethane (1.08 ml) was added and stirring was continued for 2 h. The mixture was treated with acetic acid (10 ml) and water (10 ml), poured into saturated potassium carbonate solution (200 ml) and extracted with ethyl acetate (2×100 ml). The combined, dried organic extracts were filtered and evaporated to give a yellow foam (11.3 g). FCC (column made up of EtOAc:Et₃N 99:1) eluting with ethyl acetate gave the title compound (5.0 g) as a white solid, m.p. 209°–210°.

INTERMEDIATE 22

3-[5-Methyl-1-(triphenylmethyl)-1H-imidazol-4-yl]-1-[1-(2-propenyl)-1H-indol-3-yl]-1-propanone A suspension of Intermediate 19 (500 mg) in dry DMF (3 ml) was added dropwise to a stirred suspension of sodium hydride (40 mg, 73% in oil) in dry DMF (1 ml) under nitrogen. After 15 min allyl bromide (0.105 ml) was added and the mixture stirred for 18 h. Water (50 ml) was added and the solution extracted with dichloromethane (3×25 ml). The combined extracts were dried, filtered and evaporated to give a viscous gum (685 mg). Column chromatography on silica gel (Merck 7734; made up in ethyl acetate:triethylamine (99:1) with ethyl acetate as the eluent gave the title compound (245 mg) as a yellow foam, t.l.c. on Et₃N impregnated SiO₂ (ethyl acetate), Rf 0.28.

Intermediates 23 to 27 were prepared in a similar manner from Intermediate 19 and the appropriate alkylating agent. Similar column chromatography and t.l.c. conditions were used.

INTERMEDIATE 23

1-[1-(1-Methylethyl)-1H-indol-3-yl]-3-[5-methyl-1-(triphenylmethyl)-1H-imidazol-4-yl]-1-propanone (740 mg) as a yellow foam, t.l.c. Rf 0.35, from Intermediate 19 (1.0 g) and isopropyl iodide (0.24 ml) with a reaction time of 16 h.

INTERMEDIATE 24

1-(1-Cyclopentyl-1H-indol-3-yl)-3-[5-methyl-1-(triphenylmethyl)-1H-imidazol-4-yl]-1-propanone (370 mg) as a yellow foam, t.l.c. Rf 0.40, from Intermediate 19 (500 mg) and cyclopentylbromide (0.13 ml) with a reaction time of 29 h.

INTERMEDIATE 25

1-(1-Cyclopentylmethyl-1H-indol-3-yl)-3-[5-methyl-1-(triphenylmethyl)-1H-imidazol-4-yl]-1-propanone (365 mg) as a yellow foam, t.l.c. Rf 0.40, from Intermediate 19 (500 mg) and cyclopentanemethanol (4-methylbenzenesulphonate) (305 mg) with a reaction time of 22 h.

INTERMEDIATE 26

3-[5-Methyl-1-(triphenylmethyl)-1H-imidazol-4-yl]-1-(1-phenylmethyl-1H-indol-3-yl)-1-propanone (175 mg) as a white solid, m.p. 186°–188°, from Intermediate 19 (500 mg) and benzyl bromide (0.14 ml) with a reaction time of 20 h.

INTERMEDIATE 27

3-[5-Methyl-1-(triphenylmethyl)-1H-imidazol-4-yl]-1-[1-(2-propynyl)-1H-indol-3-yl]-1-propanone (37 mg) as a yellow foam, t.l.c. Rf 0.37, from Intermediate 19 (250 mg), potassium carbonate (138 mg) (instead of sodium hydride) and propargyl bromide (0.045 ml) in acetone with a reaction time of 96 h.

INTERMEDIATE 28

(E)-1-(1-Methyl-1H-indol-3-yl)-3-[5-methyl-1-(triphenylmethyl)-1H-imidazol-4-yl]-2-propen-1-one A mixture of 5-methyl-1-(triphenylmethyl)-1H-imidazole-4-carboxaldehyde (2.5 g), 1-(1-methyl-1H-indol-3-yl)-1-ethanone (1.0 g) and potassium hydroxide (3.1 g) in absolute ethanol (50 ml) and water (25 ml) was stirred at room temperature for 72 h, then at 50° for 18 h. The mixture was partitioned between 2N sodium carbonate (200 ml) and ethyl acetate (2×200 ml) and the combined organic layers were washed with brine (150 ml), dried and evaporated in vacuo to leave a foam (3.9 g) which was purified by FCC eluting with ethyl acetate:hexane (1:1) to give the title compound (1.76 g) as a solid, m.p. 216°–219°.

INTERMEDIATE 29

1-Methyl-[3-[3-(5-methyl-1H-imidazol-4-yl)propyl]]-1H-indole maleate

Diisobutyl aluminium hydride (1.0M in hexane, 1.1 ml) was added to a stirred, cold (−60°) solution of 3-(5-methyl-1H-imidazol-4-yl)-1-(1-methyl-1H-indol-3-yl)-1-propanone (0.83 g) in dry THF (40 ml) under nitrogen. After 1 h, the mixture had warmed to 0°, and was quenched with brine (50 ml). Dichloromethane (300 ml) was added and the mixture was filtered. The organic layer of the filtrate was dried and evaporated in vacuo to leave an orange oil (ca. 1 g). This oil was purified by FCC eluting with System A (92.5:7.5:0.75) to give the free base of the title compound (0.3 g) as an orange gum. This gum was dissolved in ethanol (5 ml), and treated with a solution of maleic acid (160 mg) in hot ethanol (1 ml). The mixture was evaporated and dissolved in hot ethyl acetate (100 ml). Further purification by FCC eluting with System A (94.5:5:0.5) gave the free base of the title compound (60 mg) as a yellow oil. This oil was dissolved in ethyl acetate (15 ml), and a solution of maleic acid (32 mg) in ethyl acetate (1 ml) was added. Dilution with dry ether (15 ml) and cooling to 4° overnight gave the title compound (75 mg) as white crystals, m.p. 84°–85°.

INTERMEDIATE 30

4-(Chloromethyl)-5-methyl-1-(triphenylmethyl)-1H-imidazole

A solution of thionyl chloride (1.3 ml) in dry dichloromethane (10 ml) was added over 5 min to a stirred suspension of 5-methyl-1-(triphenylmethyl)-1H-imidazole-4-methanol (5.0 g) in a mixture of dichloromethane (100 ml) and dry DMF (2 ml) at 0°. The mixture was stirred at 0° for 0.5 h and washed consecutively with 8% sodium bicarbonate (2×50 ml), water (50 ml), dried and evaporated in vacuo below 40° to give an oil (5 g). This was dissolved in ether (100 ml) and the resulting solution filtered through a pad of silica which was further eluted with ether (2×100 ml). The combined filtrates were evaporated below 40° to give a white foam which was triturated with cold hexane and filtered to give the title compound (4.2 g) as a white crystalline solid, m.p. 133°–135°.

EXAMPLE 1

3-(1H-Imidazol-4-yl)-1-(1-methyl-1H-indol-3-yl)-1-propanone maleate

Phosphorus oxychloride (10 ml) was added over 5 min to N,N-dimethyl-3-(1H-imidazol-4-yl)-1-propanamide hydrochloride (750 mg) under nitrogen at 0°. The reaction mixture was stirred and heated at 40° for 1 h, and the excess phosphorus oxychloride was removed by evaporation in vacuo. 1,2-Dichloromethane (30 ml) was added followed by 1-methylindole (0.47 ml) and the mixture was heated under nitrogen at reflux for 1 h. The mixture was cooled and phosphorus oxychloride (0.34 ml) was added. It was then stirred for 0.5 h and heated at reflux for 2 h. The cooled reaction mixture was poured onto ice (ca. 150 ml) and stirred overnight. The aqueous solution was washed with dichloromethane (2×75 ml; discarded), basified with 2N sodium carbonate and extracted with dichloromethane (3×75 ml). The combined, dried organic extracts were evaporated in vacuo to give a foam (0.64 g). This was dissolved in absolute ethanol (25 ml), and maleic acid (323 mg) in methanol (3 ml) was added with stirring. Dry ether (ca. 25 ml) was added, precipitating the crystalline title compound (842 mg) after drying (pistol, 76°, 18 h), m.p. 158°–161°.

Analysis Found: C, 61,5; H, 5.1; N, 11.3; $C_{15}H_{15}N_3O.C_4H_4O_4$ requires C, 61.8; H, 5.2; N, 11.4%.

EXAMPLE 2

3-(1H-Imidazol-4-yl)-1-(1,2-dimethyl-1H-indol-3-yl)-1-propanone maleate

Phosphorus oxychloride (0.10 ml) was added to a mixture of N,N-dimethyl-3-(1H-imidazol-4-yl)propanamide hydrochloride (220 mg) and 1,2-dimethylindole (142 mg) and the mixture was heated at 85° for 20 h. Cold water (40 ml) was added and the cooled mixture was washed with dichloromethane (2×20 ml; discarded), basified with 2N sodium carbonate and extracted with dichloromethane (4×20 ml). The combined, dried organic extracts were evaporated to yield a foam (0.22 g). This was purified by FCC eluting with System A (89:10:1) to give the free base of the title compound (160 mg) as a yellow oil. This was dissolved in ethanol (20 ml), and maleic acid (70 mg) in ethanol (2 ml) was added. The solution was evaporated and the solid residue crystallised from ethanol (8 ml) to give the title compound (173 mg) as white crystals, m.p. 143°–144°.

Analysis Found: C, 62.2; H, 5.8; N, 10.7; $C_{16}H_{17}N_3O.C_4H_4O_4.1C_2H_5OH$ requires C, 62.5; H, 5.6; N, 10.8%.

EXAMPLE 3

3-(5-Methyl-1H-imidazol-4-yl)-1-(1-methyl-1H-indol-3-yl)-1-propanone maleate

A mixture of N,N-dimethyl-3-(5-methyl-1H-imidazol-4-yl)propanamide dihydrochloride (1.8 g), 1-methylindole (1.12 g) and phosphorus oxychloride (1.01 ml) was stirred at 85° under nitrogen for 1.75 h. The mixture was cooled and water (ca. 60 ml) was added. The aqueous solution was washed with dichloromethane (2×30 ml; discarded), basified with 2N sodium carbonate (to pH 9) and extracted with dichloromethane (3×40 ml). The combined organic extracts were evaporated in vacuo to give a gum (1.33 g). Maleate formation as in Example 22 gave the title compound (1.3 g) as a solid, m.p. 150°–153°. This material was identical to the product from Example 22 by t.l.c.

EXAMPLE 4

3-(5-Methyl-1H-imidazol-4-yl)-1-(1,2-dimethyl-1H-indol-3-yl)-1-propanone maleate A mixture of N,N-dimethyl-3-(5-methyl-1H-imidazol-4-yl)propanamide dihydrochloride (393 mg), 1,2-dimethylindole (270 mg) and phosphorus oxychloride (0.19 ml) was heated at 85° in a closed vessel for 3 h. The mixture was cooled and cold water (50 ml) was added. The aqueous solution was washed with dichloromethane (2×50 ml; discarded), basified with 2N sodium carbonate and extracted with ethyl acetate (5×150 ml). The combined, dried organic extracts were evaporated to yield the free base of the title compound as an oily solid (470 mg). This was purified by FCC eluting with System A (89:10:1) to give the free base of the title compound (438 mg) as an oily solid. This was dissolved in hot ethanol (50 ml), and maleic acid (198 mg) in warm ethanol (5 ml) was added. The solution was evaporated and the residual solid was crystallised from ethanol (20 ml) to give the title compound (448 mg) as white crystals, m.p. 170°–171°.

Analysis Found: C, 63.4; H, 5.8; N, 10.6; $C_{17}H_{19}N_3O.C_4H_4O_4$ requires C, 63.5; H, 5.8; N, 10.6%.

EXAMPLE 5

3-(5-Methyl-1H-imidazol-4-yl)-1-(1-methyl-2-phenyl-1H-indol-3-yl)-1-propanone maleate A solution of N,N-dimethyl-3-(5-methyl-1H-imidazol-4-yl)propanamide (250 mg) in ethanol (10 ml) was acidified (to pH 1) by the addition of ethanolic hydrogen chloride. The yellow solution was evaporated and the residual oil triturated with ether (10 ml) and evaporated to give N,N-dimethyl-3-(5-methyl-1H-imidazol-4-yl)propanamide dihydrochloride as white crystals. 1-Methyl-2-phenylindole (343 mg) and phosphorus oxychloride (0.19 ml) were added and the mixture heated at 85° for 1.5 h. The mixture was cooled, water (60 ml) was added and the aqueous solution was washed with dichloromethane (2×50 ml; discarded), basified with 2N sodium carbonate (to pH 10) and extracted with ethyl acetate (2×85 ml). The combined, dried organic extracts were evaporated to give a yellow oil. This was purified by SPCC eluting with System A (956:40:4) to give the free base of the title compound (193 mg) as a yellow oil (183 mg). This yellow oil was dissolved in hot ethanol (20 ml), and maleic acid (67 mg) in ethanol (3 ml) was added. The solution was evaporated and the residual solid was crystallised from ethanol to give the title compound (153 mg) as a white powder, m.p. 166°–167°.

Analysis Found: C, 67.9; H, 5.5; N, 9.1; $C_{22}H_{21}N_3O.C_4H_4O_4$ requires C, 68.0; H, 5.5; N, 9.1%.

EXAMPLE 6

3-(2-Methyl-1H-imidazol-4-yl)-1-(1-methyl-1H-indol-3-yl)-1-propanone maleate

Phosphorus oxychloride (10 ml) was added dropwise over 15 min to N,N-dimethyl-3-(2-methyl-1H-imidazol-4-yl)propanamide hydrochloride (250 mg) at 0° under nitrogen and the mixture stirred at 40° for 1.25 h. The resulting suspension was evaporated in vacuo while protecting from atmospheric water, and dry 1,2-dichloroethane (20 ml) followed by further phosphorus oxychloride (0.10 ml) were added to the remaining solid. The mixture was heated under nitrogen to 80° and 1-methylindole (0.15 ml) added. The reaction was heated under reflux for 3 h, cooled, poured onto ice (ca. 150 ml) and left overnight. 2N Hydrochloric acid (20 ml) and dichloromethane (75 ml) were added to the resulting mixture and the layers separated. The aqueous layer was basified with saturated potassium carbonate and extracted with dichloromethane (3×100 ml). These combined organic layers were dried and evaporated in vacuo to gived a foam (0.2 g). This foam was dissolved in ethanol (5 ml), and a solution of maleic acid (108 mg) in ethanol (1.5 ml) was added with stirring. Addition of ethyl acetate (5 ml) precipitated the crystalline title compound (220 mg), m.p. 166°–168°.

Analysis Found: C, 62.5; H, 5.4; N, 10.8; $C_{16}H_{17}N_3O.C_4H_4O_4$ requires C, 62.65; H, 5.5; N, 11.0%.

EXAMPLE 7

1-(1-Methyl-1H-indol-3-yl)-3-(5-propyl-1H-imidazol-4-yl)-1-propanone maleate

A solution of N,N-dimethyl-3-(5-propyl-1H-imidazol-4-yl)propanamide (500 mg) in dichloromethane (5 ml) was treated with an excess of ethereal hydrogen chloride. The solvent was removed in vacuo and the residue triturated with dry ether (3×10 ml) to leave a viscous gum. 1-Methylindole (0.31 ml) and phosphorus oxychloride (0.26 ml) were added and the mixture heated at 80° for 1.5 h. Water (50 ml) was added and the suspension was washed with dichloromethane (2×50 ml; discarded), basified with 2N sodium carbonate (to pH 9) and extracted with dichloromethane (3×50 ml). The combined, dried organic extracts were evaporated to give a yellow foam (ca. 600 mg). FCC eluting with Sytem A (200:10:1) gave a yellow foam (330 mg). This was dissolved in ethanol (ca. 5 ml), and maleic acid (132 mg) in ethanol (ca. 1.5 ml) was added. The solvent was removed in vacuo and the residue triturated with dry ether (3×10 ml) to give the title compound (420 mg) as a solid, m.p. 144°–146°.

Analysis Found: C, 64.1; H, 6.2; N, 10.0; $C_{18}H_{21}N_3O.C_4H_4O_4$ requires C, 64.2; H, 6.1; N, 10.2%.

EXAMPLE 8

2,2-Dimethyl-3-(5-methyl-1H-imidazol-4-yl)-1-(1-methyl-1H-indol-3-yl) 1-propanone maleate Lithium diisopropylamide mono(tetrahydrofuran) (1.5M in cyclohexane, 2.55 ml) was added dropwise to a cold (−70°) solution of 2-methyl-1-(1-methyl-1H-indol-3-yl)-3-[5-methyl-1-(triphenylmethyl)-1H-imidazol-4-yl]-1-propanone (2.0 g) in dry THF (40 ml) under nitrogen. Hexamethylphosphoramide (0.665 ml) was added and the stirred solution was allowed to warm to 20° over 1.5 h. The solution was cooled (−70°) and iodomethane (0.24 ml) was added. The mixture was allowed to warm to 0° over 1 h and was stirred at this temperature for 2 h. Acetic acid (4 ml) and water (4 ml) were added and the mixture was poured into saturated potassium carbonate solution (80 ml) and extracted with ethyl acetate (2×40 ml). The combined, dried organic extracts were filtered and evaporated to give a yellow oil (ca. 3.5 g). The crude material was dissolved in acetic acid (25 ml), water (25 ml) and THF (25 ml) and heated at reflux for 2 h. The THF was removed in vacuo, the residual suspension was dissolved in 1N hydrochloric acid (200 ml) and washed with ethyl acetate (2×100 ml). The combined organic layers were extracted with 1N hydrochloric acid (100 ml) and then discarded. The combined aqueous layers were basified (to pH 9) with potassium carbonate and extracted with dichloromethane (3×100 ml). The combined extracts were dried, filtered and evaporated to give a dark green oil (ca. 2 g). SPCC eluting with System A (200:10:1) gave a yellow foam (670 mg). This material was dissolved in dichloromethane (ca. 5 ml) and a solution of maleic acid (267 mg) in ethanol (ca. 2 ml) was added. The solvent was removed in vacuo and the residue triturated with dry ether (3×20 ml) to give the title compound (805 mg) as a white solid, m.p. 119°–120°.

Analysis Found: C, 64.3; H, 6.1; N, 10.0; $C_{18}H_{21}N_3O.C_4H_4O_4$ requires C, 64.2; H, 6.1; N, 10.2%.

EXAMPLE 9

2-Methyl-3-(5-methyl-1H-imidazol-4-yl)-1-(1-methyl-1H-indol-3-yl)-1-propanone maleate A solution of lithium diisopropylamide was made by the addition of n-butyllithium (1.56M in hexane, 0.64 ml) to a cold (0°) solution of diisopropylamine (0.07 ml) in dry THF (9.3 ml). A portion of this solution (9.3 ml) was added to a stirred cold (−70°) solution of 1-(1-methyl-1H-indol-3-yl)-3-[5-methyl-1-(triphenylmethyl)-1H-imidazol-4-yl]-1-propanone (0.5 g) in dry THF (10 ml) under nitrogen. The resulting mixture was stirred at −70° for 1 h and allowed to warm to 20° (ca. 1 h). The mixture was then cooled to −70° and treated with iodomethane (0.1 ml) stirred for 1 h and allowed to warm to 20°. A further portion of iodomethane (0.1 ml) was added and the mixture was stirred at 20° for 2 h and then quenched with acetic acid (10 ml) and water (10 ml). The acidic mixture was partitioned between saturated potassium carbonate solution (60 ml) and ethyl acetate (2×60 ml). The combined, dried organic extracts were evaporated to give a brown gum (0.5 g), which was purified by SPCC eluting with ethyl acetate:methanol:triethylamine (80:20:1) to give a white foam (0.33 g). This was dissolved in a mixture of acetic acid (9 ml) and water (9 ml) and heated on a steam bath for 2.5 h. The resulting mixture was cooled to 20° and partitioned between ethyl acetate (3×60 ml) and saturated potassium carbonate solution (60 ml). The combined, dried organic extracts were evaporated to leave a brown gum (0.35 g) which was purified by FCC eluting with System A (100:8:1) to give a white foam. This foam was dissolved in ethyl acetate (12 ml) and treated with a solution of maleic acid (27 mg) in ethyl acetate (3 ml) to precipitate the title compound (0.09 g) as a white solid, m.p. 161°–163°.

Analysis Found: C, 63.3; H, 5.9; N, 10.3; $C_{17}H_{19}N_3O.C_4H_4O_4$ requires C, 63.5; H, 5.8; N, 10.6%.

EXAMPLE 10

3-(1-Methyl-1H-imidazol-4-yl)-1-(1-methyl-1H-indol-3-yl)-1-propanone maleate 3-(1H-Imidazol-4-yl)-1-(1-methyl-1H-indol-3-yl)-1-propanone maleate (440 mg) was partitioned between 8% sodium hydrogen carbonate (75 ml) and chloroform (3×50 ml) and the combined, dried organic layers were evaporated in vacuo to leave a foam (300 mg). This foam was dissolved in dry DMF (15 ml) at 0° under nitrogen and sodium hydride (42 mg, 78% in oil) was added with stirring. After 15 min, methyl iodide (0.075 ml) was added and stirring was continued for 1 h at 0°. Saturated sodium hydrogen carbonate (10 ml) was added and the resulting suspension partitioned between water (75 ml) and chloroform (3×75 ml). The combined, dried organic layers were evaporated in vacuo and the residual gum was purified by FCC eluting with System A (94.5:5:0.5) followed by high pressure liquid chromatography (h.p.l.c.) (5 $\mu$m Hypersil column 25 cm×4.6 mm) eluting with n-hexane:chloroform:ethanol (100:100:10)+0.1% $NH_4OH$ to give a gum (118 mg) as the first eluted u.v. active component. This gum was dissolved in absolute ethanol (1.5 ml), and a solution of maleic acid (54 mg) in absolute ethanol (0.5 ml) was added. Dilution with ethyl acetate (ca. 4 ml) precipitated the title compound (113 mg) as a crystalline solid, m.p. 136°–137°.

Analysis Found: C, 62.4; H, 5.5; N, 10.8; $C_{16}H_{17}N_3O.C_4H_4O_4$ requires C, 62.6; H, 5.5; N, 11.0%.

EXAMPLE 11

3-(1-Methyl-1H-imidazol-5-yl)-1-(1-methyl-1H-indol-3-yl)-1-propanone maleate

The h.p.l.c. of Example 10 gave a solid (83 mg) as the second eluted u.v. active compound. This solid was dissolved in absolute ethanol (1.5 ml), filtered, and a solution of maleic acid (38 mg) in absolute ethanol (0.5 ml) was added. Dilution with ethyl acetate (ca. 4 ml) precipitated the title compound (80 mg) as a crystalline solid, m.p. 157°–158°.

Analysis Found: C, 62.2; H, 5.4; N, 10.7; $C_{16}H_{17}N_3O.C_4H_4O_4$ requires C, 62.6; H, 5.5; N, 11.0%.

EXAMPLES 12a AND 12b 1-(1-Methyl-1H-indol-3-yl)-3-[5-methyl-1-(2-propenyl)-1H-imidazol-4-yl]-1-propanone maleate (12a) and 1-(1-Methyl-1H-indol-3-yl)-3-[4-methyl-1-(2-propenyl)-1H-imidazol-5-yl]-1-propanone maleate (12b)

A solution of 3-(5-methyl-1H-imidazol-4-yl)-1-(1-methyl-1H-indol-3-yl)-1-propanone (500 mg) in dry DMF (3 ml) was added dropwise to a stirred suspension of sodium hydride (74 mg, 73% in oil) in dry DMF (1.5 ml). After 20 min allyl bromide (0.16 ml) was added and the mixture was stirred under nitrogen for 1.5 h. Water (50 ml) was added and the suspension extracted with dichloromethane (3×25 ml). The combined dried organic extracts were filtered and evaporated to give a yellow oil (ca. 800 mg). FCC eluting with System A (400:10:1) gave a mixture of the free bases of the title compounds (12a) and (12b) (310 mg) as a brown oil. Purification by h.p.l.c. (Zorbax 7-8 $\mu$m silica, 250×21.2 mm column) eluting with chloroform:n-hexane:methanol (200:40:15)+0.4% water gave the separated free bases of the title compounds (12a) (166 mg) and (12b) (62 mg) respectively. Maleate formation from each of these compounds as in Example 8 gave the title compound (12a) (162 mg) as a solid, m.p. 105°–106°.

Analysis Found: C, 64.95; H, 5.95; N, 9.81; $C_{19}H_{21}N_3O.C_4H_4O_4$ requires C, 65.23; H, 5.95; N, 9.92%; and the title compound (12b) (67 mg) as a solid, m.p. 108°–109°.

Water Analysis Found: 0.76% w/w≡0.17 mol $H_2O$
Analysis Found: C, 64.7; H, 6.0; N, 9.6; $C_{19}H_{21}N_3O.C_4H_4O_4.0.13H_2O$ requires C, 64.8; H, 6.0; N, 9.85%.

EXAMPLES 13a AND 13b 1-(1-Methyl-1H-indol-3-yl)-3-[5-methyl-1-(phenylmethyl)-1H-imidazol-4-yl]-1-propanone maleate (13a) and 1-(1-Methyl-1H-indol-3-yl)-3-[4-methyl-1-(phenylmethyl)-1H-imidazol-5-yl]-1-propanone maleate (13b)

Examples (13a) and (13b) were prepared from 3-(5-methyl-1H-imidazol-4-yl)-1-(1-methyl-1H-indol-3-yl)-1-propanone (500 mg) and benzyl bromide (0.22 ml) using the method of Examples (12a) and (12b) Similar FCC and t.l.c. conditions were used, to give a mixture of the free bases of the title compounds (13a and 13b) (470 mg) as a yellow foam. Purification by h.p.l.c. (using the conditions of Examples (12a) and (12b)) gave the separated free bases of the title compounds (13a) (275 mg) and (13b) (113 mg) respectively. Maleate formation from each of these compounds as in Example 8 gave the title colmpound (13a) (317 mg) as a solid, m.p. 128°–129°.

Analysis Found: C, 68.37; H, 5.79; N, 8.70; $C_{23}H_{23}N_3O.C_4H_4O_4$ requires C, 68.48; H, 5.75; N, 8.87%; and the title compound (13b) (121 mg) as a solid, m.p. 138°–140°.

Water Analysis Found: 0.92% w/w≡0.24 mol $H_2O$
Analysis Found: C, 67.9; H, 5.9; N, 8.7; $C_{23}H_{23}N_3O.C_4H_4O_4.0.24H_2O$ requires C, 67.9; H, 5.8; N, 8.8%.

EXAMPLE 14

3-(5-Methyl-1H-imidazol-4-yl)-1-(1H-indol-3-yl)-1-propanone maleate

A solution of 3-[5-methyl-1-(triphenylmethyl)-1H-imidazol-4-yl]-1-(1H-indol-3-yl)-1-propanone (370 mg) in acetic acid (10 ml), water (10 ml) and THF (10 ml) was heated at reflux for 1 h. The solution was poured into 1N hydrochloric acid (50 ml) and washed with ethyl acetate (50 ml; discarded). The aqueous layer was basified with potassium carbonate (to pH~9) and extracted with dichloromethane (3×50 ml). The combined, dried organic extracts were filtered and evaporated to give a yellow solid (130 mg). This was dissolved in ethanol (3 ml), and maleic acid (62 mg) in ethanol (0.5 ml) was added. The solvent was removed in vacuo and the residue triturated with dry ether (4×10 ml) to give the title compound (173 mg) as a white solid, m.p. 125°.

Analysis Found: C, 61.3; H, 5.4; N, 10.8; $C_{15}H_{15}N_3O.C_4H_4O_4.0.2C_2H_5OH$ requires C, 61.6; H, 5.3; N, 11.1%.

Examples 15 to 21 were prepared in a similar manner from the appropriate protected intermediates.

EXAMPLE 15

3-(5-Methyl-1H-imidazol-4-yl)-1-[1-(2-propenyl)-1H-indol-3-yl]-1-propanone maleate The deprotection of 3-[5-methyl-1-(triphenylmethyl)-1H-imidazol-4-yl]-1-[1-(2-propenyl)-1H-indol-3-yl]-1-propanone (215 mg) gave the title compound (80 mg) as a pale brown solid, m.p. 142°–144°.

Analysis Found: C, 64.7; H, 5.9; N, 9.9; $C_{18}H_{19}N_3O.C_4H_4O_4$ requires C, 64.5; H, 5.7; N, 10.3%.

EXAMPLE 16

1-[1-(1-Methylethyl)-1H-indol-3-yl]-3-(5-methyl-1H-imidazol-4-yl)-1-propanone maleate The deprotection of 1-[1-(1-methylethyl)-1H-indol-3-yl]-3-[5-methyl-1-(triphenylmethyl)-1H-imidazol-4-yl]-1-propanone (670 mg) gave the title compound (295 mg) as a pale brown solid, m.p. 148°–150°.

Analysis Found: C, 64.2; H, 6.1; N, 10.1; $C_{18}H_{21}N_3O.C_4H_4O_4$ requires C, 64.2; H, 6.1; H, 10.2%.

EXAMPLE 17

1-(1-Cyclopentyl-1H-indol-3-yl)-3-(5-methyl-1H-imidazol-4-yl)-1-propanone maleate The deprotection of 1-(1-cyclopentyl-1H-indol-3-yl)-3-[5-methyl-1-(triphenylmethyl)-1H-imidazol-4-yl]-1-propanone (340 mg) gave the title compound (120 mg) as a white solid, m.p. 86°–89°, t.l.c. (System A 200:10:1), Rf 0.33.

EXAMPLE 18

1-(1-Cyclopentylmethyl-1H-indol-3-yl)-3-(5-methyl-1H-imidazol-4-yl)-1-propanone maleate The deprotection of 1-(1-cyclopentylmethyl-1H-indol-3-yl)-3-[5-methyl-1-(triphenylmethyl)-1H-imidazol-4-yl]-1-propanone (300 mg) gave the title compound (87 mg) as a solid, m.p. 158°–160°.

Water Analysis Found: 0.285% w/w≡0.072 mol $H_2O$

Analysis Found: C, 65.9; H, 6.4; N, 9.4; $C_{21}H_{25}N_3O.C_4H_4O_4.0.072H_2O$ requires C, 66.3; H, 6.5; N, 9.3%.

EXAMPLE 19

3-(5-Methyl-1H-imidazol-4-yl)-1-[1-(phenylmethyl)-1H-indol-3-yl]-1-propanone maleate The deprotection of 3-[5-methyl-1-(triphenylmethyl)-1H-imidazol-4-yl]-1-[1-(phenylmethyl)-1H-indol-3-yl]-1-propanone (160 mg) gave, after purification of the combined products of the dichloromethane extracts (37 mg) and the ethyl acetate wash (150 mg) by column chromatography on silica gel (Merck 7734; made up in EtOAc:MeOH:Et$_3$N 90:9:1) eluting with ethyl acetate:methanol (9:1), a colourless oil (83 mg). Maleate formation gave the title compound (100 mg) as a white solid, m.p. 145°–147°, t.l.c. on Et$_3$N impregnated SiO$_2$ (EtOAc:MeOH 9:1), Rf 0.39.

EXAMPLE 20

3-(5-Methyl-1H-imidazol-4-yl)-1-[1-(2-propynyl)-1H-indol-3-yl]-1-propanone maleate The deprotection of 3-[5-methyl-1-(triphenylmethyl)-1H-imidazol-4-yl]-1-[1-(2-propynyl)-1H-indol-3-yl]-1-propanone (30 mg) using the method of Example 14, but adding the reaction mixture to saturated potassium carbonate solution gave, after purification of the product of the dichloromethane extracts (30 mg) by FCC eluting with System A (150:10:1), a brown oil (10 mg). Maleate formation gave the title compound (6 mg) as a solid, m.p. 155°–158°, t.l.c. (System A 150:10:1), Rf. 0.22.

EXAMPLE 21

(E)-3-(5-Methyl-1H-imidazol-4-yl)-1-(1-methyl-1H-indol-3-yl)-2-propen-1-one maleate The deprotection of (E)-1-(1-methyl-1H-indol-3-yl)-3-[5-methyl-1-(triphenylmethyl)-1H-imidazol-4-yl]-2-propen-1-one (300 mg) was effected using the method of Example 14, with the exception that the reaction mixture was poured into 0.1N hydrochloric acid and extracted with ethyl acetate. Maleate formation followed by the addition of ethyl acetate, precipitated the title compound (195 mg) as yellow crystals, m.p. 190°–192°, t.l.c. (ethyl acetate:hexane 1:1), Rf 0.6.

EXAMPLE 22

3-(5-Methyl-1H-imidazol-4-yl)-1-(1-methyl-1H-indol-3-yl)-1-propanone maleate

A solution of (E)-1-(1-methyl-1H-indol-3-yl)-3-[5-methyl-1-(triphenylmethyl)-1H-imidazol-4-yl]-2-propen-1-one (1.4 g) in ethyl acetate (150 ml) and ethanol (50 ml) was added to a previously hydrogenated suspension of 10% palladium on carbon (140 mg of a 50% paste with water) in ethanol (50 ml) and was stirred under hydrogen for 64 h. The reaction mixture was filtered through Hyflo, evaporated in vacuo and the residual gum was triturated with hexane (100 ml). The residue was treated with ethyl acetate (5 ml) followed by hexane (100 ml), and the resulting precipitate was filtered off. This solid was dissolved in THF (7 ml), acetic acid (7 ml) and water (7 ml), heated at reflux for 1 h and the cooled solution was partitioned between 1N hydrochloric acid (2×100 ml) and ethyl acetate (100 ml). The aqueous layers were basified with potassium carbonate (to pH 9), and extracted with dichloromethane (3×100 ml). The combined, dried organic extracts were evaporated in vacuo to give a solid (0.75 g). This solid was dissolved in hot ethanol (25 ml) and chloroform (10 ml), and maleic acid (340 mg) in ethanol (10 ml) was added. The solution was concentrated in vacuo to ca. 15 ml and diluted with ether to give the crystalline title compound (0.85 g), m.p. 155°–156°, t.l.c. (System A 89:10:1), Rf. 0.22.

Water Analysis Found: 0.62% w/w≡0.13 mol $H_2O$

Analysis Found: C, 61.9; H, 5.3; N, 10.9; $C_{16}H_{17}N_3O.C_4H_4.0.13H_2O$ requires C, 62.3; H, 5.5; N, 10.9%.

Further concentration in vacuo of the mother liquors gave further title compound (40 mg) as a solid, m.p. 153°–156°.

EXAMPLE 23

3-(5-Methyl-1H-imidazol-4-yl)-1-(1-methyl-1H-indol-3-yl)-1-propanone

1-Methyl-[3-[3-(5-methyl-1H-imidazol-4-yl)propyl]]-1H-indole maleate (15 mg) was partitioned between 2N sodium carbonate (10 ml) and dichloromethane (3×10 ml). The combined, dried organic layers were evaporated in vacuo to leave a clear gum. To a stirred solution of this gum in 10% aqueous THF (2 ml) was added a solution of 2,3-dichloro-5,6-dicyano-1,4-benzoquinone in dry THF (0.8 ml), dropwise at −10° to −15° under nitrogen. After 1.5 h the reaction mixture was evaporated in vacuo and purified by FCC eluting with System A (94.5:5:0.5) to give the title compound (6.7 mg) as a gum, t.l.c. (System A 89:10:1), Rf. 0.27.

N.m.r. δ (CDCl$_3$) 2.20 (3H, s, C=C—CH$_3$), 2.98 (2H, m, CH$_2$—Im), 3.20 (2H, m, CH$_2$—CO—), 3.83 (3H, s, N—CH$_3$), 7.30–7.38 and 8.38 (3H, m and 1H, m respectively, benzene ring protons), 7.42 (1H, s, CH=N of imidazole), 7.73 (1H, s, N—CH of indole).

EXAMPLE 24

3-(5-Methyl-1H-imidazol-4-yl)-1-(1-methyl-1H-indol-3-yl)-1-propanone maleate n-Butyllithium (1.58M in hexane, 4.1 ml) was added at −78° under nitrogen to a stirred solution of diisopropylamine (0.9 ml) in dry THF (25 ml) and the solution was stirred at 0° for 0.5 h. The solution was cooled to −78° and added via a cannula to a stirred solution of 3-acetyl-1-methylindole (928 mg) in dry THF (5 ml) at −78° under nitrogen. After 0.5 h at −78° the solution was stirred at 0° for 0.5 h, cooled to −78° and a solution of 4-(chloromethyl)-5-methyl-1-(triphenylmethyl)-1H-imidazole (200 g) in dry THF (20 ml) was added dropwise with stirring under nitrogen. The solution was stirred at −78° for 1 h and at 0° for 2 h, poured into cold 8% aqueous sodium bicarbonate (100 ml) and extracted with ethyl acetate (2×100 ml). The combined, dried organic extracts were evaporated to give an orange oil (ca. 3 g) which was treated with a mixture of glacial acetic acid (40 ml), water (40 ml) and THF and heated at reflux for 1 h. The solution was evaporated and treated with 1N hydrochloric acid (70 ml). It was then washed with ethyl acetate (70 ml-discarded), basified with 2N sodium carbonate (to pH 11) and extracted with dichloromethane (4×130 ml). The combined, dried organic extracts were evaporated to give a brown foam (350 mg) which was purified by SPCC eluting with System A (923:70:7) to give the free base of the title compound as a pale yellow oil (81 mg). Maleate formation was in Example 22, but using ethanol alone as the solvent gave the title compound (50 mg) as a solid, m.p. 148°–150°. This material was identical to the product from Example 22 by t.l.c.

EXAMPLE 25

3-(5-Methyl-1H-imidazol-4-yl)-1-(1,7-dimethyl-1H-indol-3-yl)propanone maleate

A solution of N,N-dimethyl-3-(5-methyl-1H-imidazol-4-yl)-1-propanamide (300 mg) in ethanol (15 ml) was acidified (to pH 1) by the addition of ethanolic hydrogen chloride, and evaporated to yield an oil which was triturated with ether to give N,N-dimethyl-3-(5-methyl-1H-imidazol-4-yl)-1-propanamide dihydrochloride (270 mg) as a powder. This was added to a mixture of 1,7-dimethylindole (195 mg) and phosphorus oxychloride (0.15 ml) and the mixture was heated at 85° in a 'closed vessel' for 1.5 h. The mixture was cooled, cold water (50 ml) was added and the suspension was stirred for 0.5 h. It was then washed with ethyl acetate (2×40 ml; discarded), basified with 2N sodium carbonate and extracted with ethyl acetate (4×80 ml). The combined, dried organic extracts were evaporated to give the free base of the title compound (232 mg) as a solid which was dissolved in hot ethanol (15 ml), and maleic acid (105 mg) in warm ethanol (5 ml) was added. The solution was evaporated and the residual solid was crystallised from ethanol (15 ml) to give the title compound (235 mg), m.p. 164°–165°.

Analysis Found: C, 63.4; H, 5.9; N, 10.5. $C_{17}H_{19}N_3O.C_4H_4O_4$ requires C, 63.5; H, 5.8; N, 10.6%.

Examples 26, 27, 28 and 29 were prepared in a similar manner to Example 25.

EXAMPLE 26

3-(5-Methyl-1H-imidazole-4-yl)-1-(1,6-dimethyl-1H-indol-3-yl)propanone maleate

N,N-Dimethyl-3-(5-methyl-1H-imidazol-4-yl)-1-propanamide (255 mg) was converted to its dihydrochloride and reacted with 1,6-dimethyl-1H-indole (250 mg) and phosphorus oxychloride (0.19 ml) at 85° for 2.5 h. Work-up and salt formation gave the title compound (247 mg), m.p. 167°–168°.

Analysis Found: C, 63.3; H, 5.9; N, 10.4. $C_{17}H_{19}N_3O.C_4H_4O_4$ requires C, 63.5; H, 5.8; N, 10.6%.

EXAMPLE 27

3-(5-Methyl-1H-imidazol-4-yl)-1-(5-fluoro-1-methyl-1H-indol-3-yl)propanone maleate The reaction of N,N-dimethyl-3-(5-methyl-1H-imidazol-4yl)-1-propanamide dihydrochloride (505 mg), 5-fluoro-1-methyl-1H-indole (350 mg) and phosphorus oxychloride (0.23 ml) followed by work-up and salt formation gave the title compound (483 mg), m.p. 172°–173°.

Analysis Found: C, 59.9; H, 5.1; N, 10.3. $C_{16}H_{16}FN_3O.C_4H_4O_4$ requires C, 59.9; H, 5.0; N, 10.5%.

EXAMPLE 28

3(5-Methyl-1H-imidazol-4-yl)-1-(1,5-dimethyl-1H-indol-3-yl)propanone maleate

The reaction of N,N-dimethyl-3-(5-methyl-1H-imidazol-4-yl)-1-propanamide dihydrochloride (317 mg), 1,5-dimethyl-1H-indole (220 mg) and phosphorus oxychloride (0.17 ml) followed by work-up and salt formation gave the title compound (327 mg), m.p. 168°–169°.

Analysis Found: C, 63.2; H, 5.8; N, 10.7. $C_{17}H_{19}N_3O.C_4H_4O_4$ requires C, 63.5; H, 5.8; N, 10.6%.

EXAMPLE 29

3-(1H-Imidazol-4-yl)-1-(5-fluoro-1-methyl-1H-indol-3-yl)propanone maleate

The reaction of N,N-dimethyl-3-(1H-imidazol-4-yl)-1-propanamide hydrochloride (220 mg), and 5-fluoro-1-methyl-1H-indole (146 mg) and phosphorus oxychloride (0.10 ml) followed by work-up and salt formation gave the title compound (200 mg). Further recrystallisation from ethanol (8 ml) gave the title compound (120 mg), m.p. 153°–154°.

Analysis Found: C, 58.7; H, 4.7; N, 10.6. $C_{15}H_{14}FN_3O.C_4H_4O_4$ requires C, 58.9; H, 4.7; N, 10.4%.

EXAMPLE 30

1-(1-Methyoxycarbonyl-1H-indol-3-yl)-3-(5-methyl-1H-imidazol-4-yl)-1-propanone maleate A suspension of 3-[5-methyl-1-(triphenylmethyl)-1H-imidazol-4-yl]-1-(1H-indol-3-yl)-1-propanone (500 mg) in dry DMF (3 ml) was added dropwise to a stirred suspension of sodium hydride (73% dispersion in oil; 40 mg) in dry DMF (1 ml) under nitrogen. After 15 min. methyl chloroformate (0.093 ml) was added and the mixture was stirred for 4.5 h. Water (50 ml) was added and the suspension was extracted with dichloromethane (3×25 ml). The combined, dried organic extracts were evaporated to give an oil (ca. 710 mg) which was purified by FCC (column made up in ethyl acetate:hexane:- triethylamine 80:19:1) eluting with ethyl acetate:hexane (4:1) to give a foam (320 mg). This was dissolved in a mixture of dry THF (9 ml), acetic acid (9 ml) and water (9 ml) and heated at reflux for 1 h. The mixture was poured into saturated potassium carbonate solution (60 ml) and extracted with dichloromethane (3×30 ml). The combined, dried organic extracts were dried to give a solid (288 mg) which was purified by FCC eluting with System A (200:10:1) to give a solid (174 mg). This was dissolved in ethanol (2 ml) and treated with a solution of maleic acid (68 mg) in ethanol (0.5 ml). The solvent was removed in vacuo and the residue was triturated with dry ether (3×5 ml) to give the title compound (180 mg), m.p. 167°–169°.

Water assay: Found 1.38% w/w≡0.33 mol $H_2O$.

Analysis: Found: C, 58.0; H, 4.9; N, 9.5. $C_{17}H_{17}N_3O_3 \cdot C_4H_4O_4 \cdot 0.33H_2O$ requires C, 58.2; H, 5.0; N, 9.7%.

EXAMPLE 31

N,N-dimethyl-3-[3-(5-methyl-1H-imidazol-4-yl)-1-oxopropyl]-1H-indole-1-carboxamide maleate (i)

N,N-Dimethyl-3-[3-[5-methyl-1-(triphenylmethyl)-1H-imidazol-4-yl]-1-oxopropyl]-1H-indole-1-carboxamide A solution of 3-[5-methyl-1-(triphenylmethyl)-1H-imidazol-4-yl]-1-(1H-indol-3-yl)-1-propanone (500 mg) in dry DMF (3 ml) was added dropwise to a stirred suspension of sodium hydride (73% dispersion in oil; 40 mg) in dry DMF (1 ml) under nitrogen. After 15 min. dimethylcarbamyl chloride (0.11 ml) was added and the mixture was stirred for 20 h. Water (50 ml) was added and the suspension was extracted with dichloromethane (3×25 ml). The combined, dried organic extracts were evaporated to give an oil (815 mg) which was purified by FCC (column made up in ethyl acetate:triethylamine 99:1) eluting with ethyl acetate to give the title compound (445 mg) as a foam, t.l.c. on triethylamine impregnated silica (ethyl acetate) Rf 0.20.

(ii)

N,N-Dimethyl-3-[3-(5-methyl-1H-imidazol-4-yl)-1-oxopropyl]-1H-indole-1-carboxamide maleate A solution of N,N-dimethyl-3-[3-[5-methyl-1-(triphenylmethyl)-1H-imidazol-4-yl]-1-oxopropyl]-1H-indole-1-carboxamide (400 mg) in a mixture of acetic acid (12 ml), water (12 ml) and THF (12 ml) was heated at reflux for 3 h. The mixture was poured into saturated potassium carbonate solution (80 ml) and extracted with dichloromethane (3×40 ml). The combined, dried organic extracts were evaporated to give a gum (420 mg) which was purified by FCC eluting with System A (200:10:1) to give an oil (200 mg). This was dissolved in ethanol (ca. 3 ml) and treated with a solution of maleic acid (75 mg) in ethanol (ca. 1 ml). The solvent was removed in vacuo and the residue was triturated with dry ether (5×5 ml) to give the title compound (218 mg), m.p. 129°–130°.

Analysis Found: C, 59.9; H, 5.7; N, 12.4. $C_{18}H_{20}N_4O_2 \cdot C_4H_4O_4$ requires C, 60.0; H, 5.5; N, 12.7%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Direct Compression Tablet | mg/tablet |
| --- | --- |
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

Tablets of other strengths may be prepared by altering the ratio of active ingredient to excipients or the compression weight and using punches to suit.

| CAPSULES | mg/capsule |
| --- | --- |
| Active Ingredient | 0.5 |
| *Starch 1500 | 98.5 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

SYRUP

This may be either a sucrose or sucrose free presentation.

| Sucrose-Free Syrup | mg/5 ml dose |
| --- | --- |
| Active Ingredient | 0.5 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTION FOR INTRAVENOUS ADMINISTRATION

| | mg/ml | |
| --- | --- | --- |
| Active ingredient | 0.05 | 0.5 |

| | mg/ml | |
|---|---|---|
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:

1. A compound of formula (I):

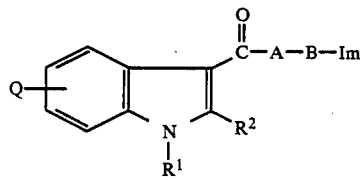

or a physiologically acceptable salt or solvate thereof, wherein Im represents an imidazolyl group of formula:

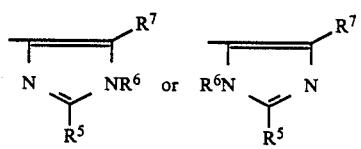

$R^1$ represents a hydrogen atom, or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, $-CO_2R^8$, $-COR^8$, $-CONR^8R^9$ or $-SO_2R^8$ (wherein $R^8$ and $R^9$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is unsubstituted or substituted by one or more $C_{1-4}$alkyl, $C_{1-4}$alkoxy or hydroxy groups or halogen atoms, with the proviso that $R^8$ does not represent a hydrogen atom when $R^1$ represents a group $-CO_2R^8$ or $-SO_2R^8$);

$R^2$ represents a hydrogen atom or a $C_{1-6}$alkyl, $C_{3-6}$alkenyl, $C_{3-7}$cycloalkyl, phenyl or phenyl$C_{1-3}$alkyl group;

A-B represents the group $R^3R^4C-CH_2$ or $R^3C=CH$; $R^3$ and $R^4$, which may be the same or different, each represents a hydrogen atom or a $C_{1-6}$alkyl group;

one of the groups represented by $R^5$, $R^6$ and $R^7$ represents a hydrogen atom or a $C_{1-6}$alkyl, $C_{3-7}$cycloalkyl, $C_{3-6}$alkenyl, phenyl or phenyl$C_{1-3}$alkyl group, and each of the other two groups which may be the same or different, represents a hydrogen atom or a $C_{1-6}$alkyl group;

Q represents a hydrogen or a halogen atom or a hydroxy, $C_{1-4}$alkoxy, phenyl$C_{1-3}$alkoxy or $C_{1-6}$alkyl group or a group $-NR^{10}R^{11}$ or $CONR^{10}R^{11}$ (wherein $R^{10}$ and $R^{11}$, which may be the same or different, each represents a hydrogen atom or a $C_{1-4}$alkyl or $C_{3-4}$alkenyl group, or together with the nitrogen atom to which they are attached form a saturated 5 or 7 membered ring);

and with the proviso that when A-B represents the group $R^3C=CH$, Q represents a hydrogen atom and $R^1$ represents a hydrogen atom or a $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl or phenyl$C_{1-3}$alkyl group.

2. A compound according to claim 1 of formula (Ia):

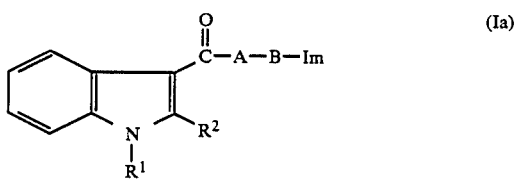

wherein $R^1$ represents a hydrogen atom or a $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl or phenyl$C_{1-3}$alkyl group; and $R^2$, A-B and Im are as defined in claim 1.

3. A compound according to claim 2 in which $R^1$ represents a hydrogen atom or a $C_{1-3}$alkyl, $C_{3-4}$alkenyl, $C_{3-4}$alkynyl, $C_{5-6}$cycloalkyl, $C_{5-6}$cycloalkylmethyl or benzyl group.

4. A compound according to claim 2 in which $R^2$ represents a hydrogen atom or a $C_{1-3}$alkyl or phenyl group.

5. A compound according to claim 2 in which A-B represents CH=CH or $R^3R^4C-CH_2$ where $R^3$ and $R^4$ each independently represent a hydrogen atom or a $C_{1-3}$alkyl group.

6. A compound according to claim 2 in which $R^5$ and $R^7$ each represent a hydrogen atom or a $C_{1-3}$alkyl group, and $R^6$ represents a hydrogen atom or a $C_{1-3}$alkyl, $C_{3-4}$alkenyl or benzyl group.

7. A compound according to claim 2 in which $R^1$ represents a hydrogen atom or a $C_{1-3}$alkyl, $C_{3-4}$alkenyl, $C_{3-4}$alkynyl, $C_{5-6}$cycloalkyl, or benzyl group; $R^2$ represents a hydrogen atom or a $C_{1-3}$alkyl group; A-B represents CH=CH or $R^3R^4C-CH_2$ where $R^3$ and $R^4$ each independently represent a hydrogen atom or a $C_{1-3}$alkyl group; and $R^5$, $R^6$ and $R^7$ each independently represent a hydrogen atom or a $C_{1-3}$alkyl group.

8. A compound according to claim 2 in which $R^1$ represents a hydrogen atom or a methyl, prop-2-enyl or cyclopentyl group; $R^2$ represents a hydrogen atom or a methyl group; A-B represents $CR^3R^4-CH_2$ where $R^3$ and $R^4$ each independently represent a hydrogen atom or a methyl group; $R^5$ and $R^6$ each represent a hydrogen atom; and $R^7$ represents a hydrogen atom or a $C_{1-3}$alkyl group.

9. A compound according to claim 2 in which A-B represents $R^3R^4C-CH_2$ and $R^1$, $R^2$, $R^3$, $R^4$, $R^5$, $R^6$ and $R^7$ are as defined in claim 2.

10. A compound according to claim 1 of formula (Ib):

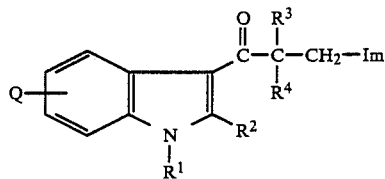

wherein $R^1$, $R^2$, $R^3$, $R^4$, Q and Im are as defined in claim 1, and with the proviso that when Q represents a hydrogen atom, $R^1$ represents $-CO_2R^8$, $-COR^8$, $-CONR^8R^9$ or $-SO_2R^8$.

11. A compound according to claim 10 in which $R^1$ represents a hydrogen atom or a $C_{1-3}$alkyl, $C_{3-4}$alkenyl, $C_{3-4}$alkynyl, $C_{5-6}$cycloalkyl, benzyl, N,N-di$C_{1-3}$alkylcarboxamido or $C_{1-3}$alkoxycarbonyl group.

12. A compound according to claim 10 in which $R^2$ represents a hydrogen atom or a $C_{1-3}$alkyl group.

13. A compound according to claim 10 in which $R^3$ and $R^4$ each independently represent a hydrogen atom or a $C_{1-3}$alkyl group.

14. A compound according to claim 10 in which $R^5$, $R^6$ and $R^7$ each represent a hydrogen atom or a $C_{1-3}$alkyl group.

15. A compound according to claim 10 in which $R^5$ and $R^6$ both represent hydrogen atoms and $R^7$ represents a $C_{1-6}$alkyl, $C_{3-7}$cycloalkyl, $C_{3-6}$alkenyl or phenyl$C_{1-3}$alkyl group.

16. A compound according to claim 10 in which Q represents a hydrogen atom, a halogen atom or a hydroxy, $C_{1-3}$alkoxy, or a $C_{1-3}$alkyl group.

17. A compound according to claim 10 in which $R^1$ represents a $C_{1-3}$alkyl, N,N-de$C_{1-3}$alkylcarboxamido or $C_{1-3}$alkoxycarbonyl group; $R^2$ represents a hydrogen atom; $R^3$ and $R^4$ both represent hydrogen atoms; $R^5$ and $R^6$ each represent a hydrogen atom; $R^7$ represents a hydrogen atom or a $C_{1-3}$alkyl group; and Q represents a hydrogen or a halogen atom or a $C_{1-3}$alkyl group.

18. A compound selected from:
3-(5-methyl-1H-imidazol-4-yl)-1-(1-methyl-1H-indol-3-yl)-1-propanone;
2-methyl-3-(5-methyl-1H-imidazol-4-yl)-1-(1-methyl-1H-indol-3-yl)-1-propanone;
3-(5-methyl-1H-imidazol-4-yl)-1-(1,2-dimethyl-1H-indol-3-yl)-1-propanone;
1-(1-methyl-1H-indol-3-yl)-3-(5-propyl-1H-imidazol-4-yl)-1-propanone;
2,2-dimethyl-3-(5-methyl-1H-imidazol-4-yl)-1-(1-methyl-1H-indol-3-yl)-1-propanone;
3-(5-methyl-1H-imidazol-4-yl)-1-(1,7-dimethyl-1H-indol-3-yl)propanone;
and physiologically acceptable salts and solvates thereof.

19. A pharmaceutical composition for the treatment of a condition selected from the psychotic disorders, anxiety, and nausea and vomiting comprising at least one compound of formula (I) as defined in claim 1 or a physiologically acceptable salt or solvate thereof in an amount effective to relieve said condition together with at least one physiologically acceptable carrier or excipient.

20. A method of treating a condition caused by disturbance of "neuronal" 5HT function which comprises administering to a patient an effective amount of a compound of formula (I) as defined in claim 1 or a physiologically acceptable salt or solvate thereof to relieve said condition.

21. A method of treating a condition selected from psychotic disorders, anxiety, and nausea and vomiting which comprises administering to a patient an effective amount to relieve said condition of a compound of formula (I) as defined in claim 1 or a physiologically acceptable salt or solvate thereof.

22. A pharmaceutical composition for the treatment of a condition selected from gastric stasis, symptoms of gastro-intestinal dysfunction, migraine and pain comprising at least one compound of formula (I) as defined in claim 1 or a physiologically acceptable salt or solvate thereof in an amount effective to relieve said condition together with at least one physiologically acceptable carrier or excipient.

23. A method of treating a condition selected from gastric stasis, symptoms of gastrointestinal dysfunction, migraine and pain which comprises administering to a patient an effective amount to relieve said condition of a compound of formula (I) as defined in claim 1 or a physiologically acceptable salt or solvate thereof.

* * * * *